United States Patent
Jehle et al.

(10) Patent No.: US 10,676,756 B2
(45) Date of Patent: Jun. 9, 2020

(54) PLANT PATTERN RECOGNITION RECEPTOR AND CHIMERAS THEREOF FOR USE AGAINST BACTERIAL INFECTIONS

(71) Applicant: EBERHARD KARLS UNIVERSITAET TUEBINGEN, Tuebingen (DE)

(72) Inventors: Anna Kristina Jehle, Tuebingen (DE); Martin Lipschis, Bremen (DE); Markus Albert, Tuebingen (DE); Georg Felix, Tuebingen (DE)

(73) Assignee: EBERHARD KARLS UNIVERSITAET TUEBINGEN, Tuebingen (DE)

( * ) Notice: Subject to any disclaimer, the term of this patent is extended or adjusted under 35 U.S.C. 154(b) by 805 days.

(21) Appl. No.: 14/404,628

(22) PCT Filed: Jun. 13, 2013

(86) PCT No.: PCT/EP2013/062254
§ 371 (c)(1),
(2) Date: Nov. 30, 2014

(87) PCT Pub. No.: WO2013/186303
PCT Pub. Date: Dec. 19, 2013

(65) Prior Publication Data
US 2017/0058292 A1    Mar. 2, 2017

(30) Foreign Application Priority Data
Jun. 13, 2012 (GB) .................................. 1210484.0

(51) Int. Cl.
| C12N 15/82 | (2006.01) |
| C07K 14/415 | (2006.01) |
| C12N 15/62 | (2006.01) |
| C07K 14/195 | (2006.01) |

(52) U.S. Cl.
CPC ........ *C12N 15/8281* (2013.01); *C07K 14/195* (2013.01); *C07K 14/415* (2013.01); *C12N 15/62* (2013.01)

(58) Field of Classification Search
None
See application file for complete search history.

(56) References Cited

FOREIGN PATENT DOCUMENTS

| WO | WO 00/20616 A1 | 4/2000 |
| WO | WO 01/09283 A2 | 2/2001 |

OTHER PUBLICATIONS

Jehle et al. The Plant Cell (2013), vol. 25, pp. 2330-2340.*
Wu et al. Nature 408:816-820 (2000).*
Albert et al. Plant Signalling and Behavior (2010), vol. 5(11), pp. 1430-1432).*
Wang et al (Plant Physiology (2008) online issue.*
Kishimoto et al (2011). Plant Signalling and Bahavior, vol. 6(3), pp. 449-451.*
Albert, Markus et al., "*Arabidopsis thaliana* Pattern Recognition Receptors for Bacterial Elongation Factor Tu and Flagellin Can Be Combined to Form Functional Chimeric Receptors," *J. Biol. Chem.*, 2010, 285(25):19035-19042.
Albert, Markus et al., "Regulation of cell behaviour by plant receptor kinases: Pattern recognition receptors as prototypical models," *European Journal of Cell Biology*, 2010, 89:200-207.
Boller, Thomas et al., "A Renaissance of Elicitors: Perception of Microbe-Associated Molecular Patterns and Danger Signals by Pattern-Recognition Receptors," *Annu. Rev. Plant Biol.*, 2009, 60:379-406.
Brunings, Asha M. et al., "*Xanthomonas citri*: breaking the surface," *Molecular Plant Pathology*, 2003, 4(3):141-157.
Database UniProt Accession No. F4HQM5 "Full-receptor like protein 1," XP002705978, 2011.
Kunze, Gernot et al., "The N Terminus of Bacterial Elongation Factor Tu Elicits Innate Immunity in *Arabidopsis* Plants," *The Plant Cell*, 2004, 16:3496-3507.
Lacombe, Séverine et al., "Interfamily transfer of a plant pattern-recognition receptor confers broad-spectrum bacterial resistance," *Nature Biotechnology*, 2010, 23(4):365-370.

* cited by examiner

*Primary Examiner* — Medina A Ibrahim
(74) *Attorney, Agent, or Firm* — Saliwanchik, Lloyd & Eisenschenk

(57) ABSTRACT

The present invention relates to the finding that an until now orphan protein named receptor-like protein 1 (RLP1) in plants mediates an immune response to bacterial infections. Specifically, the invention relates to RLP1, now named receptor of enigmatic microbe-associated molecular pattern (MAMP) of *Xanthomonas* (REMAX), in *Arabidopsis thaliana*. REMAX was found to recognise the presence of *Xanthomonas* and to initiate an immune signalling that eventually yields into a typical plant immune responses to bacterial infections. Furthermore, the invention relates to chimeric pattern recognition receptors (PRRs) composed of the extracellular domain of REMAX, which is the recognition site for sensing infection, and c-terminal portions of PRRs of other plant species. Also provided is a method to modulate the immune response of a plant to a bacterial infection by either increasing or decreasing the expression of REMAX or REMAX-like proteins, or the inventive chimeric PRRs in plants. Finally, the invention provides methods for the identification and purification of new microbe-associated molecular patterns in plants using REMAX or REMAX-like proteins and/or the novel chimeric PRRs of the present invention.

20 Claims, 5 Drawing Sheets

Figure 1:
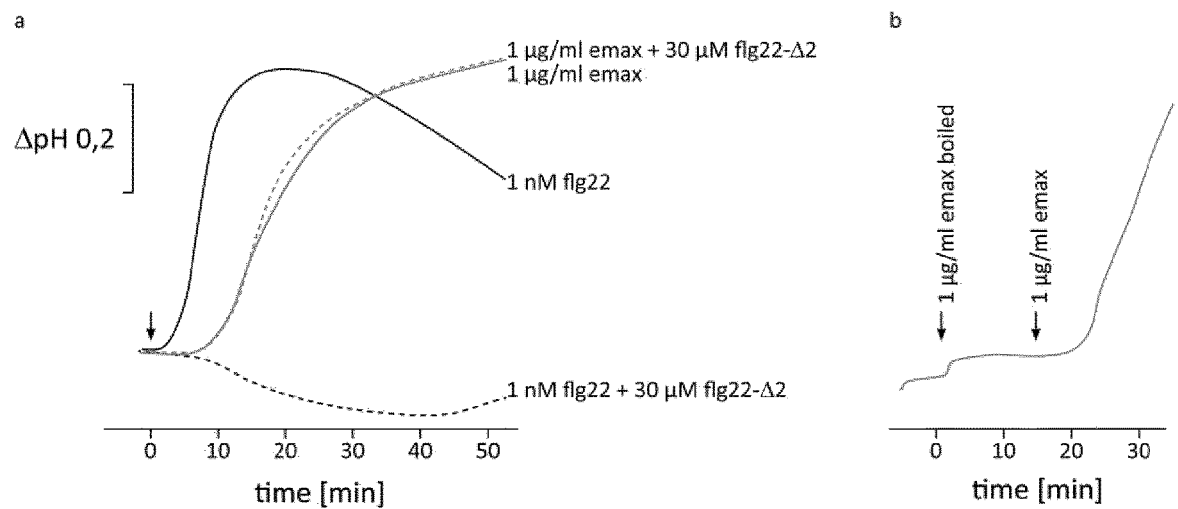

Specification includes a Sequence Listing.

Fig. 5

ReMAX (SEQ ID NO: 1)

```
SP  MRTDERRRWWVKPKKHITL
    VFITITMIIQFQMKGCVSC

NT  VETERMGLLQLKSYLKNLVDAEEEEEE
NT  GLSILKSWTHHEGDCCRWERVKCSDAIN
NT  GHVIGLSLDRLVPVAFESQTRSLNLSL

1  HSPQQSNLSWWWTNLSDHFLGFKS
 2  GTLDKLTTLDSHNMDNSLF
 3  NAATSRSLHLESNYMEVPPQE
 4  LSNMTNLRVLNLKDSSFLSSQG
 5  TDFRDLEVLDSFNGNDSEASHS
 6  ST AKLKTLDLNFPLSDFSQLKG
 7  LESLQELQVLKLRGKKNHTLSTHV
 8  KDLKMLQELDLSDGTNLDHGRG
 9  EIPTSLQVLDEKRNQLSLTHEGYLG
10  CRLMKLRELDLSSALT SLPYC
11  GNLTHLRTLDLSNQLNLSSFV
12  SGLPSVLEYLSLLDNLDSLFNS
13  VNQTRLTVFKLSSKVGVIQVQTESS
14  WAPLFQLKMLYLS CSLLSTMLGF
15  VHQRDLCFVDLSHLKLTTPTWL
16  KNNTRLQTLLLSGLSLTKLQLP
17    LVHGLQVLDLSSLMYDSLQEDI
18  GMVLPNLRFMNLSSHLQLSTLPSS
19  GELKSLQVLDLSSLGLYLQLPIMF
20  LSGCYSLRVLKLSNLQLQLKLFSK
21  HANLTGLVGLFLDGLNLTLSLEEG
22  LLKSKNLTLLDLSDNRLSLMLDLW
23  GRLSRLSYLYLSGLQLKLPLRF
24  LRQSPWLEVLDLSHLLSLSLSLDR
25  NVNLPSLRELRLQNLEPTLGLVRGN
26  LFKAAGLEVLDLRNLNLSLKLLNT
27  DQTSKLRILLLRNLSLQTYLPGK
28  CQLLSELGLLDLSHLQLRLPLPSC

ID  FSKMSFGAEQNDRTMSLVADFDFS
ID  YITFLPHCQYGSHLNLDDGVRNGY
ID  QPKPATVVDFLTKSRYEAYQ

29  GDILRYNHGLDLSSLELSLELPIE
30  GDLQNLRSLNLSSLRLTLSLPDS
31  SKLKGLESLDLSNLKLDLSLPPA
32  LADLNSLGYLNLSYNLSLELPFG

JM  HLVTFDERSYIGNAHLCGLPTNKNCIS
JM  QRVPEPPSVSTHAKEEENEEGNVIDMV
TM  WFYWTCAAVYISTSLALFAFLYI
CT  DSRWSREWFYRVDLCVHHILQFKRSSVCN
```

Eix2 (SEQ ID NO: 3)

```
SP  MGKRTNPRHFLVTWSLLLLETAFG

NT  LTSREVNKTLCIEKERGALLEFKRGLND
NT  DFGRLSTWGDEEECCNWKGIECDKRTGH
NT  VIVLDLHSEVTCPGHACFAPILTGKVSPS

1  LELEYLNFLDLSVLGLENSELRF
 2  GSLKRLEYLNLSSSDLSLELPAQ
 3  QNLTSLRILDLGNLNLIVKDLVW
 4  SHLSSLEFLRLGGLNDLQARNWFRE
 5  TKLPSLKELDLSVCGLSKFLLSPADVA
 6  NSSLISLSVLHLCCNELSTSSEYSWL
 7  NFSTSLTSLDLSHLQLSRQLDDR
 8  GSLMYLEHLNLANLFGAELGLLSS
 9  GNLTRLHYLDLSNTQTYQWLELFLRL
10  SGSRKSLEVLGLNDLSLFLSLVN
11  PRLSSLKKLYLQKLMLNLFLMER
12  GQLSSLEYLDLSDLQLRLPLPD
13  ALLPSLRELHLGSLQLQLRILPQG
14  GKLSQLRILDLSSLRLELL LES
15  GQLSNLERLDASYLVLKLTLTESH
16  SNLSSLVDLDLSFLLLSLNTRFD
17  WVPPFQLQFLRLPSCNLGPSLLKW
18  QTQNNYTLLDLSLANLSDMLLSWF
19  SNLPPELKLLNLSNLHLSLRLSEF
20  VSKQDYMILDLSSLNLSLHLL
21  VP ANLQILYLHKLHLSLSLSSIC
22  RNTLGAATSLDLSRLQLSLELLPDC
23  WMNMSNLAVLNLAYLNLSLKLPQS
24  GSLTNLEALYLRQLSLRLMLLS
25  SQCQLLQILDLGGLKLTLRLPAWI
26  GTDLLQLRILSLRSLKLDLSLLSL
27  CQLQFLQILDLSELGLSLKLLQC

ID  LNNFTILRQENGSGESMDFKVRYD
ID  YIPGSYLYIGDLLIQWKNQESEY

28  KNALLYLKILDLSSLKLVLGLLKE
29  AELRGLRSLNLSRLDLNLTLVEG
30  GQLKLLLESLDLSRLQLSLMLPQG
31  SNLTFLSVLDLSNLHLSLRLLSS

JM  TQLQSFDRSSYSGNAQLCGPPLEFCPG
JM  YAPPIDRGSNTNPQEHDDDDEFSSLE
TM  FYVSMVLGFFVTFWGILGCLIVN
CT  RSWRNAYFTFLTDMKSWLHMTSRVCF
CT  ARLKGKLR
```

PLANT PATTERN RECOGNITION RECEPTOR AND CHIMERAS THEREOF FOR USE AGAINST BACTERIAL INFECTIONS

CROSS REFERENCE TO A RELATED APPLICATION

This application is a National Stage Application of International Application Number PCT/EP2013/062254, filed Jun. 13, 2013; which claims priority to Great Britain Application No. 1210484.0, filed Jun. 13, 2012; which are incorporated herein by reference in their entirety.

The Sequence Listing for this application is labeled "SeqList-15Sep16-ST25.txt", which was created on Sep. 15, 2016, and is 30 KB. The entire content is incorporated herein by reference in its entirety.

FIELD OF THE INVENTION

The present invention relates to the finding that an until now orphan protein named receptor-like protein 1 (RLP1) in plants mediates an immune response to bacterial infections. Specifically, the invention relates to RLP1, now named receptor of enigmatic microbe-associated molecular pattern (MAMP) of *Xanthomonas* (REMAX), in *Arabidopsis thaliana*. REMAX was found to recognise the presence of *Xanthomonas* and to initiate an immune signalling that eventually yields into a typical plant immune responses to bacterial infections. Furthermore, the invention relates to chimeric pattern recognition receptors (PRRs) composed of the extracellular domain of REMAX, which is the recognition site for sensing infection, and C-terminal portions of PRRs of other plant species. Also provided is a method to modulate the immune response of a plant to a bacterial infection by either increasing or decreasing the expression of REMAX or REMAX-like proteins, or the inventive chimeric PRRs in plants. Finally, the invention provides methods for the identification and purification of new microbe-associated molecular patterns in plants using REMAX or REMAX-like proteins and/or the novel chimeric PRRs of the present invention.

DESCRIPTION

Plants are exposed to microbial pathogens but, in general, they are resistant to most of these microbes. Obviously, plants have evolved efficient barriers and defense mechanisms to successfully ward off these microbial pathogens. In turn, pathogenic microbes have found ways for entering through wounds, pores and stomata or by active penetration through the leaf or root surface. However, once inside the plant host, the pathogen encounters further preformed barriers such as the plant cell wall or antimicrobial secondary metabolites (Nürnberger and Lipka, 2005). In addition to these permanent barriers, plants have an array of inducible defense systems that come into action when plants sense attack by microbes. For pathogen detection, plants possess pattern recognition receptors (PRRs) at the plasma membrane that recognize microbe/pathogen-associated molecular patterns (MAMPs/PAMPs) via their extracellular domains and initiate intracellular signaling and induction of defense reactions. These processes are defined as PAMP-triggered immunity (PTI) (Chisholm et al., 2006; Jones and Dangl, 2006). Recognition of MAMPs induces multiple cellular responses such as altered ion fluxes across the plasma membrane causing extracellular alkalinization and increased concentrations of the cytoplasmatic Ca2+ (Boller and Felix, 2009) and biosynthesis of the stress hormone ethylene caused by the fast activation of the ACC-synthase (Spanu et al., 1994). A further early response is the induction of mitogen-activated protein kinase (MAPK) cascades causing transcriptional activation of transcription factors (Nühse et al., 2000; Asai et al., 2002). Thereby, the transcription of genes encoding proteins such as defensins (antimicrobial proteins), lytic enzymes or enzymes for the synthesis of phytoalexins (anti-microbial secondary metabolites) is induced (Nürnberger et al., 2004). Additional typical plant defense reactions are callose deposition at the plant cell wall and the production of reactive oxygen species (ROS) that can be toxic for pathogens and cause cross-linking of the plant cell wall (Apel and Hirt, 2004). To counteract PTI, some pathogens have evolved effectors that suppress this response. This process is called effector-triggered susceptibility (ETS). In turn, some plants hold specialized R (resistant) proteins that recognize these effectors. This recognition causes effector-triggered immunity (ETI) which in general leads to hypersensitive response (HR), a cell death of the plant tissue surrounding the infection site (Dangl and Holub, 1997), and thus limits the pathogen to the infection site (Chisholm et al., 2006; Jones and Dangl, 2006; Caplan et al., 2008). Many R proteins belong to the NB-LRR protein family that consists of a nucleotide binding site (NB) and a leucine-rich repeat (LRR) domain. These NB-LRRs can either interact directly with effectors via their LRR domains or indirectly via an additional protein (host factor) which binds the pathogen effector.

For initiating active defense reactions it is crucial that plant hosts can detect the attack by potential pathogens. As is the case for the well studied innate immune system of animals, plants can recognize chemical structures that are characteristic for microbial organism in general. In analogy also, these structures that serve as signals for the immune system of plants are termed MAMPs for microbe-associated molecular patterns. MAMPs often represent highly conserved molecular structures that carry essential functions for the microbes. Typically, these MAMPs are representative for whole classes of microbes but do not occur in the plant host. Recognition of MAMPs follows principles of recognition of 'non-self' (Medzhitov and Janeway, 2002; Nürnberger et al., 2004; Zipfel, 2008).

Pattern recognition receptors (PRRs) on the plant cell surface recognize MAMPs and DAMPs and transduce the signal into the cell. Until now several receptors have been identified belonging to the leucine-rich repeat receptor-like kinase (LRR-RLK) and protein (LRR-RLP) family and to the LysM-RLKs/RLPs.

The Gram-negative bacterium *Xanthomonas axonopodis* pv. *citri* (Xac) is a plant pathogen that causes citrus canker on most *Citrus* species. Originating in Asia, Xac currently causes Canker A also in South America, USA and Australia (Graham et al., 2004) with considerable economic losses (Gottwald et al., 2002). Xac enters the plant through stomata or lesions. About 9 days post infection blister-like lesions appear on the leaves that later turn brown with water-soaked margins, necrotic surrounded, becomes visible. The lesion center becomes raised and corky. Xac can also proliferate and cause similar symptoms on fruits, thus rendering the fruits unmarketable. Bacteria proliferate and exude from stomata during wet weather. Xac is then distributed mainly by wind-driven rain (Graham et al., 2004). Many members of the *Xanthomonas* genus show a high host range and race specificity with most strains restricted to a small number of hosts (Brunings and Gabriel, 2003). *Xanthomonas axonopodis* pv. *citri* is limited to *Citrus* and relatives of *Citrus* in the family Rutacea.

Several MAMPs and their corresponding pattern recognition receptors have been described so far. However, there are indications for many additional MAMPs for which the corresponding PRRs have not been identified. Some PRRs are restricted to specific plants families and a couple of MAMPs are in some microbes altered or masked, consequently are not all plants able to recognize all microbes. Therefore, transformation of PRRs to other plant species can increase the resistance to pathogens as shown for the transformation of tomato and tobacco with the PRR EFR (Lacombe et al., 2010).

In view of the above, it is an object of the present invention to provide novel means to enhance the resistance of plants to bacterial infections, specifically to infections with the pathogenic bacterium *Xanthomonas*.

In a first aspect of the present invention, the above object is solved by a chimeric pattern recognition receptor (PRR) for recognizing plant pathogen-associated molecular patterns, comprising at least an ectodomain, a juxtamembrane domain, a transmembrane domain and a cytoplasmatic domain, characterized in that the ectodomain and at least one of the other domains are derived from different PRRs.

In the context of the present invention the term "ectodomain" shall refer to the extracellular parts of a transmembrane receptor which harbour the receptor's function to bind to its ligands. Specifically, in certain embodiments of the present invention, the term "ectodomain" shall preferably refer to the LRR domain of a plant PRR.

In the context of the present invention and in all of its embodiments the term "pathogen-associated molecular patterns" shall refer to any molecular structure derived from a plant pathogenic organism and/or any other micro organism, such as bacteria, fungi or unicellular eukaryotic organisms and/or small multi-cellular organisms.

In the context of the present invention the term "transmembrane domain" shall refer to parts of a transmembrane receptor which form a stable fold in a cellular membrane. The term shall refer in case of single pass transmembrane receptors only to the domain which spans the cellular membrane. In case for multi pass transmembrane domains the term also denotes the region containing multiple single transmembrane domains.

In the context of the present invention the term "juxtamembrane domain" shall refer to the stretch of amino acids in a transmembrane receptor which is located on the extracellular side of the receptor, directly adjacent to the transmembrane domain. The juxtamembrane domain therefore connects the ectodomain with the transmembrane domain.

In a preferred embodiment the ectodomain of the chimeric receptor of the present invention is derived from the protein shown in SEQ ID No. 1, or a protein that is at least 50% identical to the protein shown in SEQ ID No. 1.

The ectodomain of the chimeric PRR according to the present invention is in another embodiment preferably derived from one PRR-PRR "A"—whereas the cytoplasmatic domain, the juxtamembrane domain and/or the transmembrane domain are derived from another (a different) PRR-PRR "B". Preferably the different PRRs ("A" and "B") are derived from different plant species.

The chimeric PRR according to the present invention is for use in the treatment and/or protection of a plant against a bacterial infection, preferably against a Xanthomonas infection.

In a further preferred embodiment the chimeric PRR of the invention comprises an ectodomain that has a sequence that is at least 50%, 60%, 70%, 80%, 90%, 95%, 98%, 99% or 100% identical to the ectodomain of REMAX—SEQ ID No. 1 or At1g07390.

Furthermore preferred is a chimeric PRR according to the invention, wherein the juxtamembrane domain, transmembrane domain and/or the cytoplasmatic domain are derived from PRRs selected from leucine-rich repeat receptor-like kinases (LRR-RLK), LRR receptor-like proteins (LRR-RLP) or LysM-RLK/RLP.

Finally, in a further embodiment of the first aspect of the present invention, the chimeric PRR, comprises a juxtamembrane domain, transmembrane domain and/or a cytoplasmatic domain which each comprise a sequence having at least 50%, 60%, 70%, 80%, 90%, 95%, 98%, 99% or 100% sequence identity to LeEix2 (SEQ ID No. 3), preferably to the c-terminal part of LeEix2, more preferably to the juxtamembrane domain, transmembrane domain and/or a cytoplasmatic domain domains of LeEix2 (SEQ ID No. 3).

The object of the present invention is furthermore solved in a second aspect by a method for modulating the resistance of a plant to a pathogen infection, comprising, modulating in said plant the expression of a protein comprising an amino acid sequence of at least 50%, 60%, 70%, 80%, 90%, 95%, 98%, 99% or 100% identity to REMAX. Preferably, wherein REMAX is a protein comprising the sequence shown in SEQ ID No. 1.

In one embodiment a method is preferred, wherein modulating constitutes either an increase or a decrease of the resistance of a plant. An increase of expression of said protein results in the increase of the resistance of said plant to a pathogen infection. The decrease of expression results in a decrease of the resistance of said plant to a pathogen infection. Most preferably the expression of said protein in said plant is increased by ectopic expression of said protein.

On the other hand, and in another preferred embodiment, the expression of said protein in said plant is decreased by mutagenesis, RNA interference or RNA mediated DNA methylation. Such techniques are well known to the person of skill in the art.

RNA mediated silencing mechanisms can interfere with gene expression at different levels: some RNA-directed mechanisms act at a post-transcriptional level through degradation of targeted messenger RNAs. However, dsRNA-derived species can also direct changes in the chromatin structure of DNA regions with which they share sequence identity. For example, plants use such RNA species to lay down cytosine methylation imprints on identical DNA sequences, providing a fundamental mark for the formation of transcriptionally silent heterochromatin. This process is generally referred to as RNA-directed DNA methylation (RdDM).

RdDM is initiated by the presence of double stranded RNA (dsRNA) molecules in the cell nucleus. They potentially trigger the de novo methylation of all cytosine bases which are located in DNA regions complementary to the sequence of the RNA double strand. As a consequence, in mammals and in plants, the methylated DNA positions serve as flags for the remodelling of the surrounding chromatin in a way, that dense heterochromatin can be formed at these loci. Due to the dense chromatin environment other proteins are prohibited from contacting the DNA. In particular transcription factors or components of the transcriptional machinery cannot assemble on the methylated promoter sequences and thus no transcription can occur in these regions. In effect, genes that have methylated regulatory sequences are less transcribed and therefore less expressed.

Preferably, the modulation of the expression of REMAX, or a REMAX-like protein or a chimeric PRR of the invention is done by RNA mediated DNA methylation targeting a sequence selected from, but is not limited to, an endogenous regulatory sequence that regulates plant DNA transcription. As used herein, the term "regulatory sequence" means a nucleotide sequence that, when operatively linked to a coding region of a gene, affects transcription of the coding region such, that a ribonucleic acid (RNA) molecule is transcribed from the coding region. A regulatory element generally can increase or decrease the amount of transcription of a nucleotide sequence, for example, a coding sequence, operatively linked to the element with respect to the level at which the nucleotide sequence would be transcribed absent the regulatory element. Regulatory elements are well known in the art and preferably include promoters, enhancers, silencers, inactivated silencer intron sequences, 3'-untranslated or 5'-untranslated sequences of transcribed sequence, preferably a poly-A signal sequence, or other protein or RNA stabilizing elements, insulators which restrict the regulatory effect of these sequences to defined regions, or other gene expression control elements known to regulate gene expression or the amount of expression of a gene product. A regulatory element can be isolated from a naturally occurring genomic DNA sequence or can be synthetic, for example, a synthetic promoter.

The terms "polynucleotide", "oligonucleotide," and "nucleic acid sequence" are used interchangeably in the context of the present invention to refer to a polymeric (two or more monomers) form of nucleotides of any length, either ribonucleotides or deoxyribonucleotides. Although nucleotides are usually joined by phosphodiester linkages, the term also includes polymers containing neutral amide backbone linkages composed of aminoethyl glycine units. The terms are used only to refer to the primary structure of the molecule. Thus, the term includes double stranded and single stranded DNA molecules as above. It will be recognized that such polynucleotides can be modified, for example, by including a label such as a radioactive, fluorescent or other tag, by methylation, by the inclusion of a cap structure, by containing a substitution of one or more of the naturally occurring nucleotides with a nucleotide analogue, by containing an internucleotide modification such as having uncharged linkages (e.g., methyl phosphonates, phosphotriesters, phosphoramidates, carbamates, or the like), by containing a pendant moiety such as a protein (e.g., a nuclease, toxin, antibody, signal peptide, poly-L-lysine, or the like), by containing an intercalator such as acridine or psoralen, by containing a chelator, which can be a metal such as boron, an oxidative metal, or a radioactive metal, by containing an alkylator, or by having a modified linkage (e.g., an alpha anomeric nucleic acid).

Preferred polynucleotide species according to the present invention are selected from ssDNA, dsDNA tDNA, ssRNA, dsRNA, shRNA, siRNA, and mRNA. Preferably, the polynucleotide is a DNA that codes for a dsRNA molecule, preferably a dsRNA-hairpin. DsRNA hairpins are preferably generated by expression of a DNA construct that encodes contiguous sense and anti-sense sequences that are separated by a spacer. Upon transcription of such a construct, the generated ssRNA molecule forms a double strand by base pairing of the sense and anti-sense sequences.

The present invention provides in a further embodiment the above method, wherein said protein is a chimeric protein comprising an ectodomain having at least 50%, 60%, 70%, 80%, 90%, 95%, 98%, 99% or 100% sequence identity to the ectodomain of REMAX (SEQ ID No. 1) and juxtamembrane domain and/or a transmembrane domain and/or a cytoplasmatic domain derived from at least one different receptor-like-protein (RLP) which is not REMAX.

A pathogen infection is preferably a bacterial infection, such as a *Xanthomonas* infection. *Xanthomonas* species in the context of all aspects and embodiments of the present invention are preferably selected from *Xanthomonas axonopodis*, *Xanthomonas campestris*, *Xanthomonas stewartii*, *Xanthomonas oryzae* and *Xanthomonas translucens*.

Plants for use in the above methods of the invention and in the context of the other aspects and embodiments of the present invention are pepper, rice, citrus, cotton, tomato, soybeans, tobacco. Preferably wherein the plant is susceptible to a Xanthomonas infection. Further plants for use in context with all aspects and embodiments of the present invention are corn (*Zea mays*), *Brassica* sp. (e.g., *B. napus, B. rapa, B. juncea*), alfalfa (*Medicago sativa*), rye (*Secale cereale*), sorghum (*Sorghum bicolor, Sorghum vulgare*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Rachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Perseaultilane*), fig (*Ficuscasica*), guava (*Psidium guava*), mango (*Mangifera indica*), olive (*Olea europaea*), papaya (*Carica papaya*), cashew (*Anacardium occidentale*), macadamia (*Macadamia integrifolia*), ahnond (*Prunus amygdalus*), sugar beets (*Beta vulgaris*), sugarcane (*Saccharum* spp.), oats, duckweed (*Lemna*), barley, tomatoes (*Lycopersicon esculentum*), lettuce (e. g., *Lactuca sativa*), green beans (*Phaseolus vulgaris*), lima beans (*Phaseoluslimensis*), peas (*Lathyrus* spp.), and members of the genus *Cucumis* such as cucumber (*C sativus*), cantaloupe (*C. cantalupensis*), and musk melon (*C. melo*). Ornamentals such as azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum* are also included. Additional ornamentals within the scope of the invention include *impatiens, Begonia, Pelargonium*, Viola, Cyclamen, *Verbena, Vinca, Tagetes*, Primula, Saint Paulia, Agertum, *Amaranthus*, Antihirrhinum, Aquilegia, *Cineraria*, Clover, Cosmo, Cowpea, Dahlia, *Datura, Delphinium*, Gerbera, Gladiolus, *Gloxinia, Hippeastrum*, Mesembryanthemum, Salpiglossos, and *Zinnia*. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsugaultilane*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*), and Alaska yellow-cedar (*Chamaecyparis nootkatensis*).

Yet another aspect of the present invention relates to a method for producing a transgenic plant having enhanced resistance to a bacterial infection, comprising the steps of (i) transforming a plant or plant cell with a nucleotide sequence encoding for a REMAX or REMAX-like protein comprising an amino acid sequence of at least 50%, 60%, 70%, 80%, 90%, 95%, 98%, 99% or 100% identity to SEQ ID No 1, or with a chimeric PRR according to invention as described herein.

It is preferred in a further embodiment that said chimeric PRR comprises a juxtamembrane domain and/or a transmembrane domain and/or a cytoplasmatic domain of an autologous PRR of said plant.

In another aspect the problem posed by the present invention is solved by providing a plant, characterized in that the plant expresses a chimeric PRR according to the invention as described herein.

In still another aspect of the present invention the objective is solved by a gene, comprising a nucleotide sequence encoding for a chimeric PRR according to the invention as described herein.

The term "gene" as used in the context of the invention describes any DNA sequence element that can be transcribed into RNA and that might encode for a heritable trait in an organism. Most genes are protein coding genes, wherein the nucleotide sequence of the gene codes for the amino acid sequence of the protein product. However, other genes might code for RNAs which are not translated into proteins—so called non-coding RNAs (ncRNAs). For example, ncRNA genes encode for transfer RNAs (tRNAs), or structural RNAs as found in large protein complexes like the ribosome (rRNAs). Further, the term "gene" includes coding regions for small none-coding RNAs species. Small non-coding RNA genes include snoRNAs, microRNAs, siRNAs and piRNAs and long ncRNAs that include examples such as Xist and HOTAIR.

Yet another aspect of the invention relates to an expression cassette characterized in that the expression cassette allows for the expression of a gene according to the invention.

A further preferred aspect of the present invention is then directed at a vector comprising a nucleic acid according to the present invention, for example a gene or an expression cassette according to the present invention. A vector within the meaning of the present invention is a protein or a nucleic acid or a mixture thereof which is capable of being introduced or of introducing the polynucleotides comprised into a cell. It is preferred that the proteins encoded by the introduced nucleic acid are expressed within the cell upon introduction of the vector.

In a preferred embodiment, the vector of the present invention comprises recombinant vectors, plasmids, phagemids, phages, cosmids, viruses, in particular but not limited to virus-derived amplicon vectors, potato virus X based vectors, tobacco rattle virus based vectors, geminivirus-based vectors such as cabbage leaf curl virus and barley stripe mosaic virus based vectors and vectors based on satellite viruses (reviewed in Curtin, S. J., Wang, M.-B., Watson, J. M., Roffey, P., Blanchard, C. L. and Waterhouse, P. M. (2007), chapter 12, p 291-332 in "Rice Functional Genomics; Challenges, Progress and Prospects". Upadhyaya, Narayana M. (Ed.), ISBN: 978-0-387-48903-2), virosomes, and nucleic acid coated particles, in particular gold spheres.

The term "recombinant nucleic acid molecule" refers to a polynucleotide produced by human intervention. A recombinant nucleic acid molecule can contain two or more nucleotide sequences that are linked in a manner such that the product is not found in a cell in nature. In particular, the two or more nucleotide sequences can be operatively linked and, for example, can encode a fusion polypeptide, or can comprise a nucleotide sequence and a regulatory element. A recombinant nucleic acid molecule also can be based on, but different, from a naturally occurring polynucleotide, for example, a polynucleotide having one or more nucleotide changes such that a first codon, which normally is found in the polynucleotide, is replaced with a degenerate codon that encodes the same or a conservative amino acid, or such that a sequence of interest is introduced into the polynucleotide, for example, a restriction endonuclease recognition site or a splice site, a promoter, a DNA replication initiation site, or the like.

Preferred is a recombinant vector according to the present invention, which is an expression vector, optionally comprising one or more genes to be expressed. Preferably, said expression is driven by a regulatory sequence (or sequences). A regulatory sequence can be isolated from a naturally occurring genomic DNA sequence or can be synthetic, for example, a synthetic promoter.

Regulatory sequences can be constitutively expressed regulatory sequences, which maintain gene expression at a relative level of activity (basal level), or can be regulated regulatory sequences. Constitutively expressed regulatory sequence can be expressed in any cell type, or can be tissue specific, which are expressed only in particular cell types, phase specific, which are expressed only during particular developmental or growth stages of a plant cell, or the like. A regulatory sequence such as a tissue specific or phase specific regulatory sequences or an inducible regulatory sequence useful in constructing a recombinant polynucleotide or in a practicing a method of the invention can be a regulatory sequence that generally, in nature, is found in a plant genome. However, the regulatory sequence also can be from an organism other than a plant, including, for example, from a plant virus, an animal virus, or a cell from an animal or other multicellular organism.

A preferred regulatory sequence useful for expression of polynucleotides of the invention is a promoter element. Useful promoters include, but are not limited to, constitutive, inducible, temporally regulated, developmentally regulated, spatially-regulated, chemically regulated, stress-responsive, tissue-specific, viral and synthetic promoters. Promoter sequences are known to be strong or weak. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. A bacterial promoter can be induced to varying levels of gene expression depending on the level of isothiopropyl galactoside added to the transformed bacterial cells. An isolated promoter sequence that is a strong promoter for heterologous nucleic acid is advantageous because it provides for a sufficient level of gene expression to allow for easy detection and selection of transformed cells and provides for a high level of gene expression when desired.

The choice of promoter will vary depending on the temporal and spatial requirements for expression, and also depending on the target species. In some cases, expression in multiple tissues is desirable. While in others, tissue-specific, e.g., leaf-specific, seed-specific, petal-specific, anther-specific, or pith-specific, expression is desirable. Although many promoters from dicotyledons have been shown to be operational in monocotyledons and vice versa, ideally dicotyledonous promoters are selected for expression in dicotyledons, and monocotyledonous promoters for expression in monocotyledons. There is, however, no restriction to the origin or source of a selected promoter. It is sufficient that the promoters are operational in driving the expression of a desired nucleotide sequence in the particular cell.

Other sequences that have been found to enhance gene expression in transgenic plants include intron sequences (e. g., from Adh 1, bronze 1, actin 1, actin 2 (WO 00/760067), or the sucrose synthase intron), poly adenylation signals in the 3' prime UTR and viral leader sequences (e.g., from TMV, MCMV and AMV). For example, a number of non-translated leader sequences derived from viruses are known to enhance expression. Specifically, leader sequences from tobacco mosaic virus (TMV), maize chlorotic mottle virus (MCMV), and alfalfa mosaic virus (AMV) have been shown to be effective in enhancing expression (e.g., Gallie et al., 1987; Skuzeski et al., 1990). Other leaders known in the art include but are not limited topicornavirus leaders, for example, EMCV leader (encephalomyocarditis virus 5'-non-coding region; Elroy-Stein et al., 1989); potyvirus leaders, for example, TEV leader (tobacco etch virus); MDMV leader (maize dwarf mosaic virus); human immunoglobulin heavy chain binding protein (BiP) leader, (Macejak et al., 1991); untranslated leader from the coat protein mRNA of AMV (AMV RNA 4; Jobling et al., 1987), TMV (Gallie et al., 1989), and MCMV (Lommel et al., 1991; see also, della Cioppa et al., 1987).

For the expression of any constructs as described herein in a plant or plant cell, the invention preferably embodies that the described polynucleotides are operable linked to a promoter and to a polyadenylation site, wherein said promoter is characterized in that it is functional in said cell of said plant. As a promoter in this context, any sequence element is sufficient that induces transcription of the downstream sequence. The minimal requirements of promoters are very well known in the art and many of such promoters are conventionally used for gene expression in plants.

In a preferred embodiment of the invention, the transformation of a plant or plant cell with any polynucleotide as described herein, is performed by a method selected from standard procedures known in the art. Transformation of plant tissue can be achieved preferably by particle bombardment (Klein et al., "High-Velocity Microprojectiles for Delivering Nucleic Acids Into Living Cells," Nature 327: 70-73 (1987)), also known as ballistic transformation of the host cell, as disclosed in U.S. Pat. Nos. 4,945,050, 5,036, 006, and 5,100,792, all to Sanford et al., and in Emerschad et al., "Somatic Embryogenesis and Plant Development from Immature Zygotic Embryos of Seedless Grapes (*Vitis vinif* era)" Plant Cell Reports 14:6-12 (1995). In particle bombardment, tungsten or gold microparticles (1 to 2 Î¼ m in diameter) are coated with the DNA of interest and then bombarded at the tissue using high pressure gas. In this way, it is possible to deliver foreign nucleotides into the nucleus. Biologically active particles (e.g., dried bacterial cells containing the vector and heterologous DNA) can also be propelled into plant cells. Other variations of particle bombardment, now known or hereafter developed, can also be used. Another preferred method of stably introducing the nucleic acid construct into plant cells is to infect a plant cell with *Agrobacterium tumefaciens* or *Agrobacterium rhizogenes* previously transformed with the polynucleotide construct. As described above, the Ti (or RI) plasmid of *Agrobacterium* enables the highly successful transfer of a foreign nucleic acid molecule into plant cells. A preferred variation of *Agrobacterium* transformation uses vacuum infiltration in which whole plants are used (Senior, "Uses of Plant Gene Silencing," Biotechnology and Genetic Engineering Reviews 15:79-119 (1998)). Yet another referred method of introduction is fusion of protoplasts with other entities, either mini-cells, cells, lysosomes, or other fusible lipid-surfaced bodies (Fraley et al., Proc. Natl. Acad. Sci. USA 79:1859-63 (1982), ). Also preferred in a method, wherein the nucleic acid molecule is introduced into the plant cells by electroporation (Fromm et al., Proc. Natl. Acad. Sci. USA 82:5824 (1985)). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. Other preferred methods of transformation include chemical-mediated plant transformation, microinjection, physical abrasives, viral transduction and laser beams (Senior, "Uses of Plant Gene Silencing," Biotechnology and Genetic Engineering Reviews 15:79-119 (1998)). The precise method of transformation is not critical to the practice of the present invention. Any method that results in efficient transformation of the host cell of choice is appropriate for practicing the present The problem of the present invention is solved in a further aspect by a screening method for identifying microbe associated molecular patterns (MAMPs), comprising the method steps of (i) expressing in a plant or plant cell or plant tissue a protein comprising an amino acid sequence of at least 50%, 60%, 70%, 80%, 90%, 95%, 98%, 99% or 100% identity to SEQ ID No 1 (REMAX), or a chimeric PRR as described herein, (ii) contacting said plant or plant cell with a candidate compound, (iii) measuring the response of said plant or plant cell, preferably the immune response, in comparison with a control plant or plant cell or plant tissue, wherein an elevated (immune) response of said plant or plant cell indicates that said candidate compound is a MAMP.

In a further embodiment, in step (iii) of the above method, the immune response of said plant or plant cell is measured by means of assessing the oxidative burst, ethylene production and/or the expression of immune responsive genes or reporter genes. Reporter genes usable in the present context are composed of an immune responsive promoter operably linked to a reporter gene which allows for an easy readout of the reporter gene expression, e.g. luciferase enzymes or fluorescent proteins. The person of skill in the art has access to a wide selection of enzymes that can be used as reporter genes.

A further aspect of the invention constitutes a method for purifying a MAMP, comprising the use of a REMAX protein, or extracellular parts thereof, such as the ectodomain, specifically the LRR domain, wherein the REMAX protein comprises a sequence of at least 50%, 60%, 70%, 80%, 90%, 95%, 98%, 99% or 100% identity to SEQ ID No. 1.

In a further embodiment in the method for purifying a MAMP, said protein is coupled to a solid carrier medium, preferably to a membrane or a bead. The purification of the MAMP can then be performed by incubating a plant extract on said membrane or bead to allow the binding of the MAMP to the receptor. Thereafter the complex is washed to remove non bound material. The MAMP then can be eluted under salt conditions which impairs the ligand-receptor binding.

The objective of the present invention is solved in an additional aspect by an elicitor of a defense reaction in a plant obtainable by a method comprising the steps of lysing *Xanthomonas* cells, binding proteins of said lysate to an anion exchange column and eluting the elicitor at low salt concentrations.

One embodiment of the invention relates to the elicitor as described above, wherein the lysing of said *Xanthomonas* cells is performed by sonication. However, in the art other methods for preparing a cellular extracts are known, like the use of chemicals such as detergents or mechanical force. It is preferred that the protocol used for lysing the cells is sufficient to allow for the releases of cellular proteins from the bacterial cells.

In one preferred embodiment the sonication is performed with a sonicator operating with an energy of at least 30 W, preferably 40 W, most preferably about 50 W. To achieve a complete lysis, the bacteria can be sonicated for multiple times, for example for at least two times, preferably three times. Bacteria are preferably cooled during the sonication. A preferred device for sonication is a SONOPLUS® HD UW2070, supplied from Bandelin, Berlin).

In another preferred embodiment of the invention, the method used to obtain the elicitor comprises a step of removing the bacterial debris from the lysed, preferably sonicated, samples. The step preferably includes a separation by centrifugation. (for example about 20 min, at about 4° C. with about 13000×g).

Even more preferably the supernatant of the above step of separation is subsequently dialyzed with a molecular weight cut off of about 2 to 10 kD, preferably 4 to 6 kD, against about 20 mM TRIS, pH8. The dialyzed material is then preferably used for loading on to an anion-exchange column.

A preferred anion exchange column for use in the present invention is a sepharose column, for example Q Sepharose, Fast Flow supplied by GE Healthcare. Preferably the column is pre-equilibrated before use.

Furthermore preferred is that in the above method the elicitor is eluted at a salt concentration of about 0 to 50%, preferably of about 0 to 40%, more preferably of about 20 to 35% most preferably of about 30% salt.

Yet another embodiment of the invention relates to the elicitor, wherein the method comprises the further steps of reloading the elicitor on an anion-exchange column and eluting with a salt gradient of 0 to 30% salt.

In one embodiment the elute from the first elution step is first dialysed a second time with a molecular weight cut off of about 2 to 10 kD, preferably 4 to 6 kD, against about 20 mM TRIS, pH8, and then re-loaded on the anion-exchange column.

In the context of the present invention the salt used for eluting the elicitor from the anion exchange column can be any salt. Preferred is however that the salt is sodium chloride (NaCl).

In one additional embodiment, the elicitor can be eluted from the second anion-exchange step using a salt gradient ranging from 0 to 30% salt, preferably NaCl, 20 mM TRIS, pH8).

The elicitor according to the present invention in a most preferred embodiment does not contain the known MAMPs Elongation factor Tu (EF-Tu) and/or flagellin.

Furthermore it is preferred that the elicitor as described herein induces an immune response in a plant, e.g. the release of ethylene, via the activation of REMAX. Therefore the elicitor of the present invention obtainable as described above is or contains in a preferred embodiment a ligand of REMAX.

In a final aspect of the present invention, a method is provided for sensitizing a plant against bacterial infections, the method comprises the steps of treating a plant, plant cell or plant tissue with the elicitor or extract according to the present invention and/or with a REMAX protein and/or receptor or chimera according to the present invention.

It has been established in the past years that plants can be sensitized to pathogenic infections. After a first attack of the pathogen it was observed that upon a second penetration such a plant displays a hypersensitive response compared to plants that had not experienced a pathogen attack before. This effect is called "priming".

Therefore, the chimeric PRRs, the methods of modulation of the resistance of a plant to pathogen infections, the elicitors or MAMPs of the present invention can be used to treat plants, plant cells or plant tissues in order to prime said plants immune system.

As used herein, the term "homologous" or "homology" denotes structural similarity between two macromolecules, particularly between two polynucleotides, irrespective of whether said similarity is or is not due to shared ancestry. Conventionally, homology denotes the level of sequence identity measured in percent. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Sambrook et al., 1989, supra.

The regeneration, development and cultivation of plants from single plant protoplast, transformants or from various transformed explants is well known in the art (Weissbach and Weissbach, In: Methods for Plant Molecular Biology, Academic Press, San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

In yet another aspect, plants derived from any method of the present invention can be used for the production of seeds, fruits, stems, roots and leaves, or other plant derived products.

The present invention will now be further described in the following examples with reference to the accompanying figures and sequences, nevertheless, without being limited thereto. For the purposes of the present invention, all references as cited herein are incorporated by reference in their entireties. In the Figures and Sequences, FIG. 1: shows the testing of emax for contamination with flagellin and EF-Tu. Extracellular alkalinization in cell cultures of *A. thaliana* wild-type cells. a. Response to flg22 and emax in the presence or absence of the flagellin antagonist flg22-Δ2 b. Alkalinization in response to boiled and non-boiled emax fraction.

Figure 2:
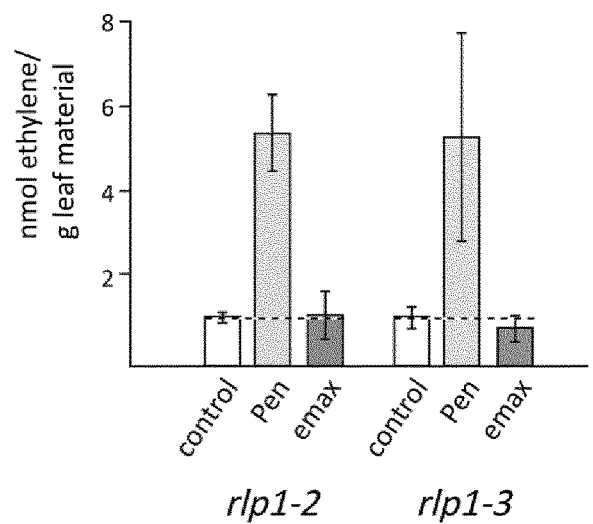

FIG. 2: shows that the lines rlp1-2 and rlp1-3 are emax-insensitive. Ethylene biosynthesis after 4 hours incubation: The T-DNA insertion lines of RLP1, rlp 1-2 and rlp 1-3, do not accumulate ethylene after emax (2 µg/ml) treatment but do respond to Pen (90 µg/ml). The bars and error bars show means and standard deviations of three replicates.

Figure 3:
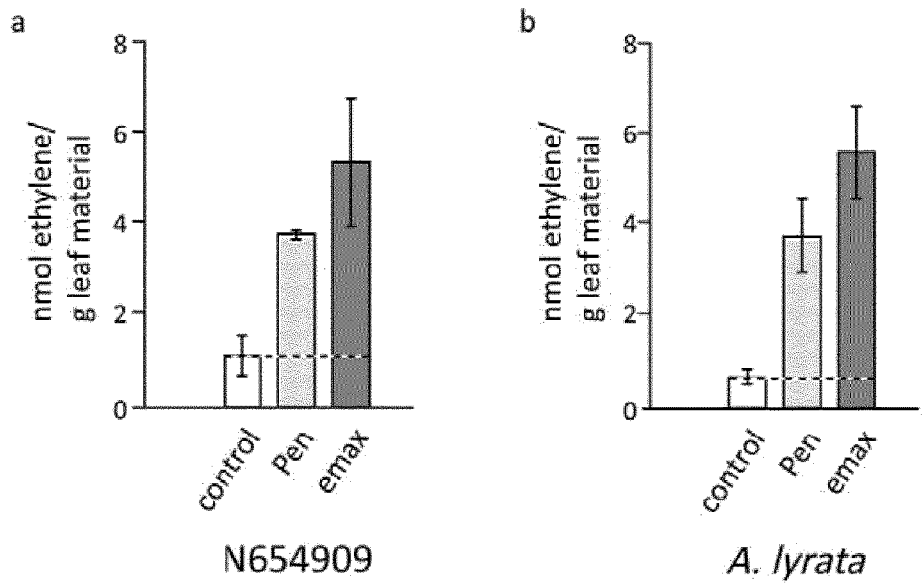

FIG. 3: shows that emax induces ethylene in the mutant of the LRR-RLK At1g06840 and *Arabidopsis lyrata*. Ethylene biosynthesis after 4 hours incubation. a. In the ethylene assay, the homozygote mutant of At1g06840 is still sensitive to emax (2 µg/ml) treatment. b. emax triggers ethylene synthesis in *Arabidopsis lyrata*, belonging to the same genus as *Arabidopsis thaliana*. As control, plants were also treated with Pen (90 µg/ml). The bars and error bars show means and standard deviations of three replicates.

Figure 4:
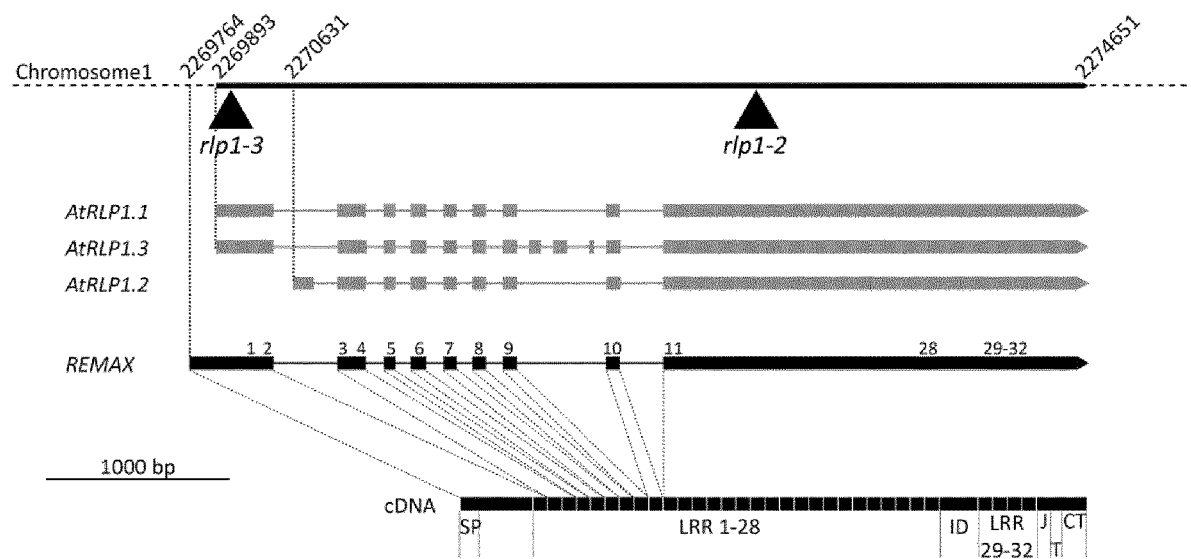

FIG. 4: shows the REMAX (RLP1) gene model and T-DNA insertions. The genomic DNA of RLP comprises almost 5000 base pairs. Three different gene models involving two different start positions have been proposed for RLP1 (www.tair.org). All three models have multiple splicing sites. The lines rlp1-2 and rlp1-3 have T-DNA insertions in exons predicted as indicated. Sequencing of Col-0 cDNA results in a fourth gene model (REMAX) that starts 129 bp upstream of the start site proposed for RLP1.1 and RLP1.3. Multiple splicing predicts an mRNA encoding a polypeptide with 1077 amino acids that has a signal peptide (SP), 32 LRRs (leucine-rich repeats) with island domain (ID), juxtamembrane domain (J), transmembrane domain (T) and a short intracellular cytoplasmatic tail (CT).

FIG. 5: shows the primary structure of REMAX and LeEix2. REMAX (a) and LeEix2 (Ron and Avni, 2004) (b) protein structures predicted from the cDNA sequences. The conserved L of the LRRS, often replaced by I, F, V or M, as well as the conserved N, G and IP, alternatively LP, FP or VP, are all highlighted in grey. The characteristic amino acids with the C-pairs at the beginning and at the end of the LRR domain are marked in black. Putative glycosylation sites in the extracellular domain with the consensus sequence NxT/S are underlined. ID: island domain, JM: juxtamembrane domain, TM: transmembrane domain, CT: cytoplasmatic tail.

Figure 6:
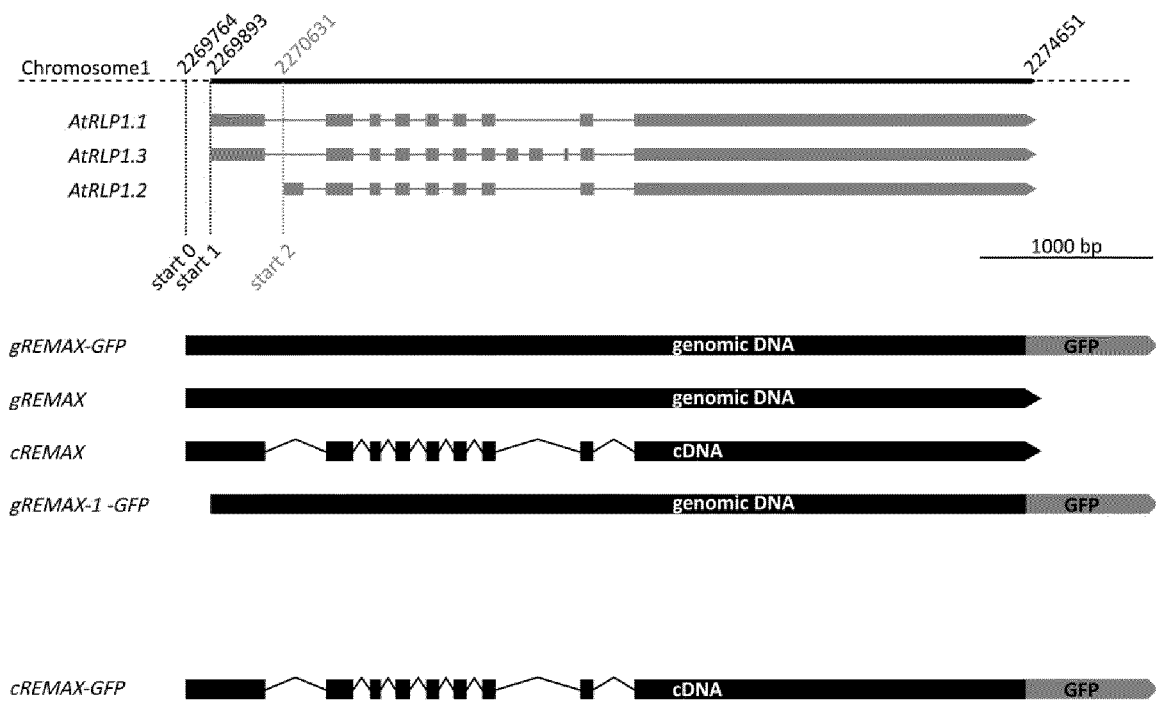

FIG. 6: shows REMAX constructs. Genomic DNA and cDNA with two different start positions (start 0 and 1) were cloned with and without C-terminal GFP-tag as indicated.

Figure 7:
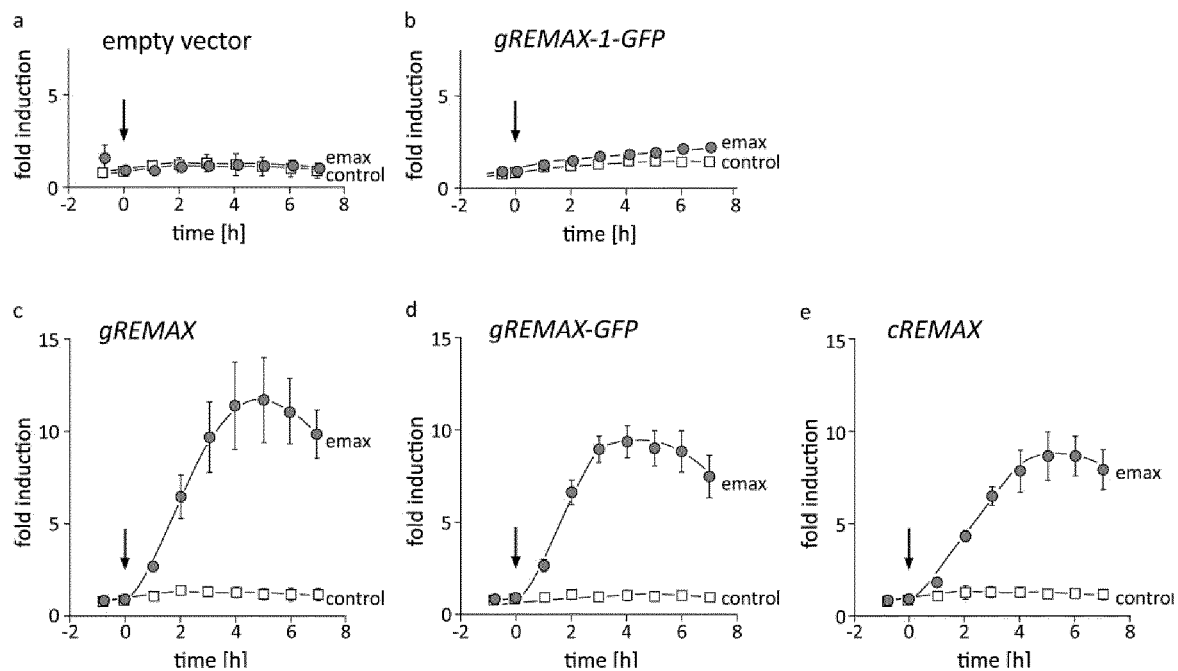

FIG. 7: shows the expression of REMAX in rlp1-2 protoplasts that restores emax response. Luciferase activity in protoplasts of rlp1-2 plants co-transformed with different REMAX constructs and a plasmid carrying luciferase under the control of the FRK1 promoter (Asai et al., 2002). The protoplasts were treated with emax (5 µg/ml) or with the inactive flg22 Atum (100 nM) as a control at time 0. Fold induction of luciferase activity was calculated with respect to values at time 0. Values represent means and standard deviations of three replicates (a, d, e, and f) or one representative out of several independent experiments (b).

Figure 8:
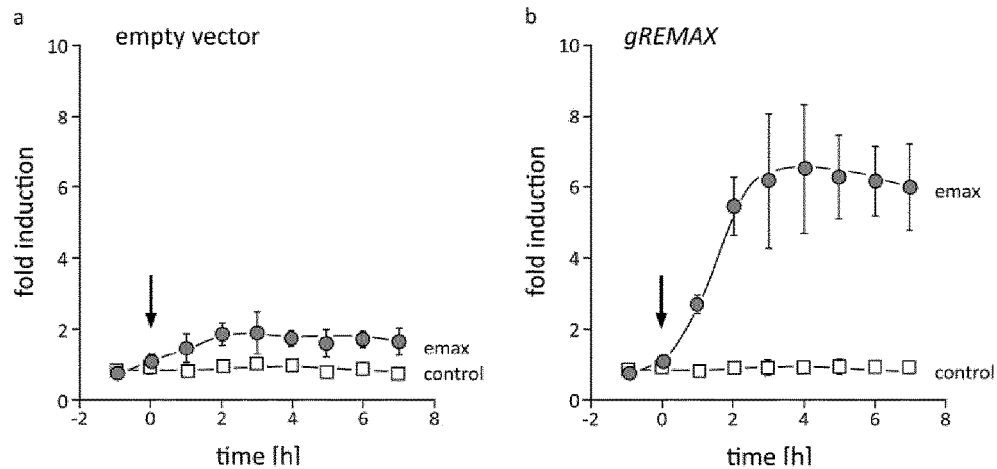

FIG. 8: shows the Transformation of Shakhdara protoplasts with REMAX restores emax function. Protoplasts from the emax-insensitive accession Sha transformed with FRK1:: luc show only slight luciferase activity after treatment with emax, while co-transformation with REMAX mediated the emax response. The protoplasts were treated with emax (5 µg/ml) or with the inactive flg22 Atum (100 nM) and fold induction of luciferase activity was calculated with respect to values at time 0. The values show means and standard deviations of three replicates.

Figure 9:
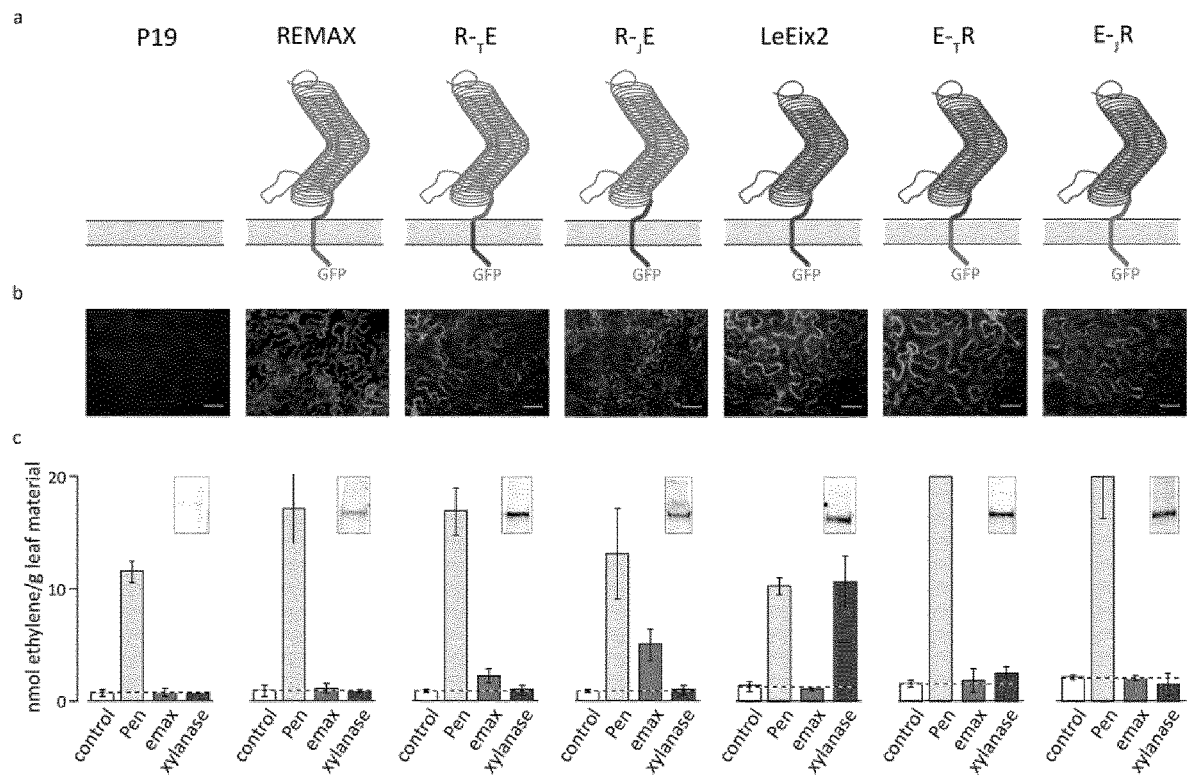

FIG. 9: shows chimeras of REMAX and LeEix2. Chimeras of REMAX and LeEix2 were created and tested for function and expression in *N. benthamiana*. a. The cartoons schematically show the different constructs. b. Expression of the chimeras in *N. benthamiana* is shown via fluorescence microscopy, (scale bar 50 µm) and c. via western blot using anti-GFP. c. The ethylene response of *N. benthamiana* expressing the different constructs induced with Pen (90 µg/ml) as positive control, emax (2 µg/ml) and xylanase (2 µg/ml) is shown after 4 hours incubation.

SEQ ID NO. 1 shows the amino acid sequence of REMAX
SEQ ID NO. 2 shows the genomic nucleic acid sequence of REMAX
SEQ ID NO. 3 shows the amino acid sequence of LeEix2
SEQ ID NO. 4 shows the nucleic acid sequence of LeEix2
SEQ ID NO: 5 shows the consensus sequence for LRR.

EXAMPLES

Example 1

*Arabidopsis thailana* Recognizes a Novel MAMP Derived from *Xanthomonas axonopodis* pv. *Citri*

Partial purified extracts of *Xanthomonas axonopodis* pv. *citri* and other *Xanthomonas* species induce MAMP responses in *Arabidopsis*. These extracts contain a MAMP, called emax for enigmatic MAMP of *Xanthomonas*, which is different from the known MAMPs flagellin, EF-Tu or peptidoglycan that are recognized from *A. thaliana* and dominant in the partial purified extracts. emax can be solubilized from different *Xanthomonas* species by sonication of the bacteria. The active protein binds to anion exchanger media and can be eluted at low salt concentrations (Q SepharoseQFast Flow, pH 8.0):

*Xanthomonas axonopodis* pv. *citri* was grown on Kings B plates (1.5% Agar) for 48 hours at 30° C. The bacteria were harvested with a spatula and 2 volumes of $H_2O$ were added. For breaking the bacterial envelope, aliquots of 30 ml of the bacterial suspension was cooled on ice and sonicated three times for two minutes (50 W, SONOPULS HD UW2070, Bandelin, Berlin,). Insoluble bacterial debris was removed by centrifugation (20 min, 4° C., 13000×g). Supernatant was extensively dialyzed (Molecular weight cut off: 4-6 kDa, Roth, Karlsruhe) against 20 mM Tris, pH 8.0 and loaded on a pre-equilibrated anion exchange column (Q Sepharose, Fast Flow, GE Healthcare, München). Emax was eluted with 30% NaCl (1 M, 250 mM Tris, pH 8.0) and after dialysis (20 mM Tris, pH 8.0, Molecular weight cut off: 4-6 kDa, Roth, Karlsruhe) reloaded on Q-Sepharose column. Elution of proteins was performed with NaCl gradient (0-30% NaCl, 20 mM Tris, pH 8.0) and tested for activity on the double mutant fls2×efr (ethylene biosynthesis or extracellular alkalinization).

While for initial characterization of the activity from *Xanthomonas* interference by the MAMPs flagellin and EF-Tu was excluded by the use of fls2×efr double mutants, further work with wild-type plants relies on absence of such MAMPs that could interfere in the assays. Active fractions eluted from anion exchange columns were pooled and tested for contamination by the known bacterial MAMPs EF-Tu and flagellin which are potent inducers of extracellular alkalinization of cell cultures as well. Flg22-Δ2, a C-terminally truncated version of flg22, has been described as a specific antagonists for flg22 in *A. thaliana* (Bauer et al., 2001). In cell cultures derived from wild-type plants, a preincubation (2 min) with the antagonist flg22-Δ2 can completely block the response of the cells to subsequent treatment with flg22 (FIG. 1*a*). In contrast, pre-treatment with flg22-Δ2 had no effect to the response observed with the fractions containing emax, indicating that flagellin is not responsible for the response observed with these fractions. To check for the presence of EF-Tu, a MAMP activity resistant to heat-treatment (Kunze et al., 2004), the inventors made use of the heat-lability of emax as a distinctive feature. Indeed, heat treatment of the emax preparation abolished all of its MAMP activity (FIG. 1b). Together, these results show that the emax preparation contained no detectable levels of flagellin or EF-Tu that could interfere with the assays.

Example 2

Mutants of RLP1 were Insensitive to Emax

Mapping with the emax-insensitive accession Shakhdara resulted in a single locus on chromosome 1. The receptor-like protein 1 (RLP1, At1g07390) is located in this region and two independent T-DNA insertion lines, rlp1-2 (SALK_116923) and rlp1-3 (SALK_049403C), were insensitive to emax. The responsiveness was tested with the increase of ethylene and the induction of the gene FRK1 (FLG22-INDUCED RECEPTOR-LIKE KINASE1, At2g19190).

Searching for homologues of RLP1 with program blastp (blast.ncbi.nlm.nih.gov/Blast.cgi) revealed clear homologues of RLP1 with >80% sequence identity only in *Arabidopsis lyrata* and *Brassica rapa*. Both species were indeed sensitive to emax treatment (FIG. 3). In summary, the close linkage between occurrence of RLP1 and response to emax renders RLP1 a likely candidate for acting as 'Receptor of emax' (REMAX).

Example 3

The Primary Structure of REMAX Comprises 32 LRRs

For the gene At1g07390 encoding REMAX/RLP1 three gene models with two different starting positions have been predicted (www.tair.de, FIG. 4). Both start sites do not encode proteins with a clear signal peptide for export (Hoeglund, A, Doennes, P, Blum, T, Adolph, H W, and Kohlbacher, O (2006). However, the open reading frame with the first start site extends to the 5' end and contains an ATG codon 129 bp further upstream. When translated from this site the protein is predicted to contain a 38 amino acid signal peptide for the secretory pathway (score of 0,96 in the MultiLoc program). The inventors tested for this prolonged version by amplifying cDNA produced from RNA of Col-0 plants with a primer encompassing this upstream start site. This cDNA exists and predicts a gene with 9 exons encoding a REMAX protein with 1077 amino acids (FIG. 4). According to this model the mature REMAX protein has a large extracellular domain consisting mainly of 32 LRRs (FIG. 5). The LRR domain is interrupted by an island domain (68 aa) between LRR 28 and LRR 29. As conserved in many other LRR domains, it is flanked on both sides by characteristic pairs of cysteine residues (Li and Chory, 1997). While many of the 32 LRRs in the N-terminal part show considerable deviations, the last four LRRs, LRRs 28-32, follow very closely the consensus sequence LxxLxxLxxLxLxxNxLxGxIPxx (SEQ ID NO: 5) (Jones et al., 1994). The extracellular domain of REMAX codes for 18 potential N-glycosylation sites (NxS/T). Between the LRR domain and the 23 amino acids long transmembrane domain, there is a juxtamembrane domain consisting of acidic amino acid residues. C-terminally, the protein has a short cytoplasmatic tail consisting of 29 amino acid residues (FIG. 5a). In general, the structure is similar to the tomato RLP LeEix2 that recognizes fungal xylanase (FIG. 5b) (Ron and Avni, 2004).

Example 4

Expression of REMAX in Protoplasts of rlp1-2 Plants Restores the Response to Emax To confirm the role of REMAX, complementation experiments with REMAX-constructs were performed in rlp 1-2 mutants (FIG. 6). REMAX-constructs based on genomic DNA or cDNA from Col-0 were co-transformed with a plasmid coding for luciferase under the control of the MAMP-inducible FRK1 promoter (Asai et al., 2002) and could restore the emax-responsiveness. These results demonstrate that REMAX is indeed required for emax perception (FIG. 7).

Furthermore, for testing functionality of REMAX in the accession Shakhdara, which showed a deletion in the region of RLP1, protoplasts derived from Shakhdara were co-transformed with FRK1::luc and REMAX and tested for luciferase activity in response to emax. This experiment clearly showed complementation of emax response by transformation of REMAX (FIG. 8).

Example 5

Chimeric Pattern Recognition Receptors Derived from REMAX

The alignment of the two RLPs REMAX and LeEix2 shows a similar overall structure of both proteins. Heterologous expression of LeEix2 in a species of tobacco that has no endogenous perception provided convincing evidence for the function of LeEix2 as the receptor for xylanase (Ron and Avni, 2004). Their large LRR-domains are subdivided by island domains inserted before the last four of the LRRs. Sequence homology between REMAX and LeEix2 is highest for these four LRRs and comprising the cysteine pair at the end of the LRR domain. Their cytoplasmatic tails show little resemblance in length or sequence.

In order to figure out whether it is the C-terminal part of these RLPs that determines functionality in *N. benthamiana* chimeric forms with swaps of their C-terminal parts were produced as summarized in FIG. 9a. The analysis of the constructs expressed in leaves of *N. benthamiana* is shown in FIG. 9c. Swapping the transmembrane domain (TM) and cytoplasmatic tail (CT) from REMAX to LeEix2, as in E-TR, rendered LeEix2 non-functional as xylanase in *N. benthamiana* cells. In contrast, *N. benthamiana* with the reciprocal receptor construct R-TE did gain responsiveness to emax. The protein part swapped between the RLPs was expanded to include also the 40 amino acid residues of the juxtamembrane domain (JM). Interestingly, when R-JE was expressed in *N. benthamiana*, a clear and significant response to emax could be detected (FIG. 9c). E-JR, in turn, was not a functional xylanase receptor in *N. benthamiana*. In summary, the C-terminal part with the juxtamembrane domain seems important for the functionality of RLPs in general and, more remarkably, it determines functionality of these receptors in different plant species.

The invention claimed is:

1. A chimeric pattern recognition receptor (PRR) that recognizes plant pathogen-associated molecular patterns of *Xanthomonas*, comprising an ectodomain, a juxtamembrane domain, a transmembrane domain and a cytoplasmatic domain, wherein at least the ectodomain that recognizes *Xanthomonas* (i) is the ectodomain of the protein shown in SEQ ID NO: 1, or (ii) is the ectodomain of a protein that is at least 90% identical to the protein shown in SEQ ID NO: 1, and
wherein at least one of the juxtamembrane domain, the transmembrane domain and the cytoplasmatic domain is the juxtamembrane domain, the transmembrane domain and the cytoplasmatic domain of the protein shown in SEQ ID NO: 3, or a protein that is at least 90% identical to the protein shown in SEQ ID NO: 3.

2. The chimeric PRR according to claim 1, wherein the ectodomain is the ectodomain of the protein shown in SEQ ID NO: 1 and the cytoplasmatic domain, the juxtamembrane domain and the transmembrane domain are the cytoplasmatic domain, the juxtamembrane domain and the transmembrane domain of the protein shown in SEQ ID NO: 3.

3. The chimeric PRR according to claim 1, wherein the ectodomain has a sequence that is at least 90% identical to the ectodomain of the protein shown in SEQ ID NO: 1, and has an activity in the treatment and/or protection of a plant against a Xanthomonas infection.

4. The chimeric PRR according to claim 1, wherein the ectodomain has a sequence that is at least 95% identical to the ectodomain of the protein shown in SEQ ID NO:1.

5. The chimeric PRR according to claim 1, wherein the juxtamembrane domain, the transmembrane domain and the cytoplasmatic domain are the juxtamembrane domain, the transmembrane domain and the cytoplasmatic domain of (i) the protein shown in SEQ ID NO: 3, or (ii) a protein that is at least 95% identical to the protein shown in SEQ ID NO: 3.

6. A method for modulating the resistance of a plant to a pathogen infection, comprising expressing in said plant the chimeric PRR according to claim 1.

7. The method according to claim 6, wherein the chimeric PRR comprises an ectodomain having at least 90% sequence identity to the ectodomain of the protein shown in SEQ ID NO:1 and the transmembrane domain and the cytoplasmatic domain of the protein shown in SEQ ID NO: 3.

8. The method according to claim 6, wherein the pathogen infection is a Xanthomonas infection.

9. The method according to claim 6, wherein the plant is selected from corn (*Zea mays*), *Brassica* sp., alfalfa (*Medicago sativa*), rye (*Secale cereal*), sorghum (*Sorghum bicolor, Sorghum vulgare*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Rachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Perseaultilane*), fig (*Ficuscasica*), guava (*Psidium guava*), mango (*Mangifera indica*), olive (*Olea europaea*), papaya (*Carica papaya*), cashew (*Anacardium occidentale*), macadamia (*Macadamia integrifolia*), ahnond (*Prunus amygdalus*), sugar beets (*Beta vulgaris*), sugarcane (*Saccharum* spp.), oats, duckweed (*Lemna*), barley, tomatoes (*Lycopersicon esculentum*), lettuce (e. g., *Lactuca sativa*), green beans (*Phaseolus vulgaris*), lima beans (*Phaseoluslimensis*), peas (*Lathyrus* spp.), Cucumis, azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrid*), carnation (*Dianthus caryophyllus*), poinsettia (*Euphorbia pulcherrima*), chrysanthemum, begonia, pelargonium, viola, cyclamen, verbena, vinca, tagetes, primula, saint paulia, agertum, amaranthus, antihirrhinum, aquilegia, cineraria, clover, cosmo, cowpea, dahlia, datura, delphinium, gerbera, gladiolus, gloxinia, hippeastrum, mesembryanthemum, salpiglossos, Zinniaand Conifers.

10. A method for producing a transgenic plant having enhanced resistance to a bacterial infection, comprising the steps of (i) transforming a plant cell with a nucleotide sequence encoding a protein selected from the group consisting of: SEQ ID NO: 1, an amino acid sequence having at least 90% identity to SEQ ID NO: 1 that recognizes *Xanthomonas*, and the chimeric PRR according to claim 1, and (ii) regenerating a transgenic plant from the transformed plant cell.

11. A plant, which expresses the chimeric PRR according to claim 1.

12. A gene, comprising a nucleotide sequence encoding the chimeric PRR according to claim 1.

13. An expression cassette comprising the gene according to claim 12.

14. A method for sensitizing a plant, plant cell or plant tissue against Xanthomonas infections, the method comprising the step of treating a plant, plant cell or plant tissue with the chimeric PRR according to claim 1.

15. The chimeric PRR according to claim 1, wherein the juxtamembrane domain (i) is the juxtamembrane domain of the protein shown in SEQ ID NO: 3, or (ii) is the juxtamembrane domain of a protein having at least 90% sequence identity to the protein shown in SEQ ID NO: 3.

16. The chimeric PRR according to claim 1, wherein the cytoplasmatic domain (i) is the cytoplasmatic domain of the protein shown in SEQ ID NO: 3, or (ii) is the cytoplasmatic domain of a protein having at least 90% sequence identity to the protein shown in SEQ ID NO: 3).

17. The chimeric PRR according to claim 1, wherein the transmembrane domain (i) is the transmembrane domain of the protein shown in SEQ ID NO: 3, or (ii) is the transmembrane domain of a protein having at least 90% sequence identity to the protein shown in SEQ ID NO: 3.

18. The chimeric PRR according to claim 1, wherein the ectodomain and the juxtamembrane domain are the ectodomain and the juxtamembrane domain of the protein shown in SEQ ID NO: 1, and the cytoplasmatic domain and the transmembrane domain are the cytoplasmatic domain and the transmembrane domain of the protein shown in SEQ ID NO: 3.

19. The chimeric PRR according to claim 1, wherein the ectodomain and the juxtamembrane domain are the ectodomain and the juxtamembrane domain of the protein shown in SEQ ID NO: 1, or of a protein that is at least 90% identical to the protein shown in SEQ ID NO: 1, and wherein the cytoplasmatic domain and the transmembrane domain are the cytoplasmatic domain and the transmembrane domain of the protein shown in SEQ ID NO: 3, or of a protein that is at least 90% identical to the protein shown in SEQ ID NO: 3.

20. The method according to claim 10, wherein the plant cell is transformed with the chimeric PRR comprising:
   i) the ectodomain of the protein shown in SEQ ID NO: 1 or the ectodomain of a protein having at least 90% sequence identity to the protein shown in SEQ ID NO: 1;
   ii) the juxtamembrane domain of the protein shown in SEQ ID NO: 3 or the juxtamembrane domain of a protein having at least 90% sequence identity to the protein shown in SEQ ID NO: 3;
   iii) the transmembrane domain of the protein shown in SEQ ID NO: 3 or the transmembrane domain of a protein having at least 90% sequence identity to the protein shown in SEQ ID NO: 3; and
   iv) the cytoplasmatic domain of the protein shown in SEQ ID NO: 3 or the cytoplasmatic domain of a protein having at least 90% sequence identity to the protein shown in SEQ ID NO: 3.

* * * * *

SEQUENCE LISTING

<160> NUMBER OF SEQ ID NOS: 5

<210> SEQ ID NO 1
<211> LENGTH: 1077
<212> TYPE: PRT
<213> ORGANISM: Arabidopsis thaliana

<400> SEQUENCE: 1

```
Met Arg Thr Asp Glu Arg Arg Trp Trp Val Lys Pro Lys Lys His
1               5                   10                  15

Ile Thr Leu Val Phe Ile Thr Ile Thr Met Ile Ile Gln Phe Gln Met
                20                  25                  30

Lys Gly Cys Val Ser Cys Val Glu Thr Glu Arg Met Gly Leu Leu Gln
            35                  40                  45

Leu Lys Ser Tyr Leu Lys Asn Leu Val Asp Ala Glu Glu Glu Glu
    50                  55                  60

Glu Gly Leu Ser Ile Leu Lys Ser Trp Thr His His Glu Gly Asp Cys
65                  70                  75                  80

Cys Arg Trp Glu Arg Val Lys Cys Ser Asp Ala Ile Asn Gly His Val
                85                  90                  95

Ile Gly Leu Ser Leu Asp Arg Leu Val Pro Val Ala Phe Glu Ser Gln
                100                 105                 110

Thr Arg Ser Leu Asn Leu Ser Leu His Ser Phe Pro Gln Leu Gln
            115                 120                 125

Ser Leu Asn Leu Ser Trp Asn Trp Phe Thr Asn Leu Ser Asp His Phe
            130                 135                 140

Leu Gly Phe Lys Ser Phe Gly Thr Leu Asp Lys Leu Thr Thr Leu Asp
145                 150                 155                 160

Phe Ser His Asn Met Phe Asp Asn Ser Ile Val Pro Phe Leu Asn Ala
                165                 170                 175

Ala Thr Ser Ile Arg Ser Leu His Leu Glu Ser Asn Tyr Met Glu Gly
                180                 185                 190

Val Phe Pro Pro Gln Glu Leu Ser Asn Met Thr Asn Leu Arg Val Leu
            195                 200                 205

Asn Leu Lys Asp Asn Ser Phe Ser Phe Leu Ser Ser Gln Gly Leu Thr
    210                 215                 220

Asp Phe Arg Asp Leu Glu Val Leu Asp Leu Ser Phe Asn Gly Val Asn
225                 230                 235                 240

Asp Ser Glu Ala Ser His Ser Leu Ser Thr Ala Lys Leu Lys Thr Leu
                245                 250                 255

Asp Leu Asn Phe Asn Pro Leu Ser Asp Phe Ser Gln Leu Lys Gly Leu
            260                 265                 270

Glu Ser Leu Gln Glu Leu Gln Val Leu Lys Leu Arg Gly Asn Lys Phe
        275                 280                 285

Asn His Thr Leu Ser Thr His Val Leu Lys Asp Leu Lys Met Leu Gln
    290                 295                 300

Glu Leu Asp Leu Ser Asp Asn Gly Phe Thr Asn Leu Asp His Gly Arg
305                 310                 315                 320

Gly Leu Glu Ile Pro Thr Ser Leu Gln Val Leu Asp Phe Lys Arg Asn
                325                 330                 335

Gln Leu Ser Leu Thr His Glu Gly Tyr Leu Gly Ile Cys Arg Leu Met
            340                 345                 350

Lys Leu Arg Glu Leu Asp Leu Ser Ser Asn Ala Leu Thr Ser Leu Pro
        355                 360                 365
```

```
Tyr Cys Leu Gly Asn Leu Thr His Leu Arg Thr Leu Asp Leu Ser Asn
    370                 375                 380

Asn Gln Leu Asn Gly Asn Leu Ser Ser Phe Val Ser Gly Leu Pro Ser
385                 390                 395                 400

Val Leu Glu Tyr Leu Ser Leu Leu Asp Asn Asn Phe Asp Gly Ser Phe
            405                 410                 415

Leu Phe Asn Ser Leu Val Asn Gln Thr Arg Leu Thr Val Phe Lys Leu
                420                 425                 430

Ser Ser Lys Val Gly Val Ile Gln Val Gln Thr Glu Ser Ser Trp Ala
            435                 440                 445

Pro Leu Phe Gln Leu Lys Met Leu Tyr Leu Ser Asn Cys Ser Leu Gly
    450                 455                 460

Ser Thr Met Leu Gly Phe Leu Val His Gln Arg Asp Leu Cys Phe Val
465                 470                 475                 480

Asp Leu Ser His Asn Lys Leu Thr Gly Thr Phe Pro Thr Trp Leu Val
                485                 490                 495

Lys Asn Asn Thr Arg Leu Gln Thr Ile Leu Leu Ser Gly Asn Ser Leu
                500                 505                 510

Thr Lys Leu Gln Leu Pro Ile Leu Val His Gly Leu Gln Val Leu Asp
        515                 520                 525

Ile Ser Ser Asn Met Ile Tyr Asp Ser Ile Gln Glu Asp Ile Gly Met
530                 535                 540

Val Phe Pro Asn Leu Arg Phe Met Asn Phe Ser Ser Asn His Phe Gln
545                 550                 555                 560

Gly Thr Ile Pro Ser Ser Ile Gly Glu Met Lys Ser Leu Gln Val Leu
            565                 570                 575

Asp Met Ser Ser Asn Gly Leu Tyr Gly Gln Leu Pro Ile Met Phe Leu
                580                 585                 590

Ser Gly Cys Tyr Ser Leu Arg Val Leu Lys Leu Ser Asn Asn Gln Leu
        595                 600                 605

Gln Gly Lys Ile Phe Ser Lys His Ala Asn Leu Thr Gly Leu Val Gly
    610                 615                 620

Leu Phe Leu Asp Gly Asn Asn Phe Thr Gly Ser Leu Glu Glu Gly Leu
625                 630                 635                 640

Leu Lys Ser Lys Asn Leu Thr Leu Leu Asp Ile Ser Asp Asn Arg Phe
                645                 650                 655

Ser Gly Met Leu Pro Leu Trp Ile Gly Arg Ile Ser Arg Leu Ser Tyr
            660                 665                 670

Leu Tyr Met Ser Gly Asn Gln Leu Lys Gly Pro Phe Pro Phe Leu Arg
        675                 680                 685

Gln Ser Pro Trp Val Glu Val Met Asp Ile Ser His Asn Ser Phe Ser
    690                 695                 700

Gly Ser Ile Pro Arg Asn Val Asn Phe Pro Ser Leu Arg Glu Leu Arg
705                 710                 715                 720

Leu Gln Asn Asn Glu Phe Thr Gly Leu Val Pro Gly Asn Leu Phe Lys
                725                 730                 735

Ala Ala Gly Leu Glu Val Leu Asp Leu Arg Asn Asn Phe Ser Gly
            740                 745                 750

Lys Ile Leu Asn Thr Ile Asp Gln Thr Ser Lys Leu Arg Ile Leu Leu
        755                 760                 765

Leu Arg Asn Asn Ser Phe Gln Thr Tyr Ile Pro Gly Lys Ile Cys Gln
    770                 775                 780
```

Leu Ser Glu Val Gly Leu Leu Asp Leu Ser His Asn Gln Phe Arg Gly
785                 790                 795                 800

Pro Ile Pro Ser Cys Phe Ser Lys Met Ser Phe Gly Ala Glu Gln Asn
            805                 810                 815

Asp Arg Thr Met Ser Leu Val Ala Asp Phe Asp Phe Ser Tyr Ile Thr
        820                 825                 830

Phe Leu Pro His Cys Gln Tyr Gly Ser His Leu Asn Leu Asp Asp Gly
    835                 840                 845

Val Arg Asn Gly Tyr Gln Pro Lys Pro Ala Thr Val Asp Phe Leu
850                 855                 860

Thr Lys Ser Arg Tyr Glu Ala Tyr Gln Gly Asp Ile Leu Arg Tyr Met
865                 870                 875                 880

His Gly Leu Asp Leu Ser Ser Asn Glu Leu Ser Gly Glu Ile Pro Ile
                885                 890                 895

Glu Ile Gly Asp Leu Gln Asn Ile Arg Ser Leu Asn Leu Ser Ser Asn
            900                 905                 910

Arg Leu Thr Gly Ser Ile Pro Asp Ser Ile Ser Lys Leu Lys Gly Leu
        915                 920                 925

Glu Ser Leu Asp Leu Ser Asn Asn Lys Leu Asp Gly Ser Ile Pro Pro
    930                 935                 940

Ala Leu Ala Asp Leu Asn Ser Leu Gly Tyr Leu Asn Ile Ser Tyr Asn
945                 950                 955                 960

Asn Leu Ser Gly Glu Ile Pro Phe Lys Gly His Leu Val Thr Phe Asp
                965                 970                 975

Glu Arg Ser Tyr Ile Gly Asn Ala His Leu Cys Gly Leu Pro Thr Asn
            980                 985                 990

Lys Asn Cys Ile Ser Gln Arg Val Pro Glu Pro Pro Ser Val Ser Thr
        995                 1000                1005

His Ala Lys Glu Glu Glu Asn Glu Glu Glu Gly Asn Val Ile Asp
    1010                1015                1020

Met Val Trp Phe Tyr Trp Thr Cys Ala Ala Val Tyr Ile Ser Thr
    1025                1030                1035

Ser Leu Ala Leu Phe Ala Phe Leu Tyr Ile Asp Ser Arg Trp Ser
    1040                1045                1050

Arg Glu Trp Phe Tyr Arg Val Asp Leu Cys Val His His Ile Leu
    1055                1060                1065

Gln Phe Lys Arg Ser Ser Val Cys Asn
    1070                1075

<210> SEQ ID NO 2
<211> LENGTH: 4891
<212> TYPE: DNA
<213> ORGANISM: Arabidopsis thaliana

<400> SEQUENCE: 2
atgagaacag acgagagaag aaggtggtgg gttaaaccga agaagcatat aactttggtg      60
ttcataacaa taacaatgat aattcaattc caaatgaaag gatgtgtaag ctgtgtggaa     120
actgaacgga tgggtttgtt gcagctcaag tcgtatctca agaatctcgt tgatgccgaa     180
gaagaagaag aagaaggact tagtattctc aagtcatgga ctcatcatga aggtgattgt     240
tgccgttggg agagagtaaa gtgtagtgat gctattaatg ccacgtcat cggtctctca      300 ctggatagac tcgtaccggt cgcatttgag tcgcaaactc ggtctttaaa tctgtctttg    360
cttcatagtt ttcctcaact ccaaagcctt aatctttcgt ggaattggtt cactaatttg    420

```
tctgatcact tccttggtac gtctctctaa ccgaacattt ctcaattttc ccactaatta    480
atgtctggat accaacaaca agaaatagcg gttcaggttt aaaccggttt taaccaaata    540
caaacaacct cacgaaaatc tcttccaacg gcaacaatag aaacagagtc cttttaccgt    600
atggttttgt ctctaagatc agccatagct gatttatcga ataagaatgt gtataaagtt    660
caatataaga tcttgatgat tgtgtgaaat aagggtaggg cgcgtgagtt tgattctgta    720
atttggtata ttacatagtg cacataaagt gttcgacagt ttgtttgaaa gagaattta    780 gtttttttt ttcccttgca ttttttgttt caggttttaa gagctttggg acactagata    840
agctcactac cttagatttc tcccataata tgttcgacaa cagtatcgtc ccgttttaa    900 atgctgcgac atcgattagg agtctacatc ttgagtctaa ttacatggaa ggtgtctttc    960
ctcctcaagg ttatgtattt cttctatatg tttggttctc tttttgacat ttttgtatat   1020
aattcaattg gagatggatt ttgacggctt cttgttctgg tgtggcagaa cttcaaaca   1080 tgacaaactt gagagtgtta aacttgaagg acaacagttt cagcttctta tcttctcaag   1140
gtaaaatatg tcaacaaacc tttatatagt tttgttgttc caaagaaaaa gagagaacta   1200
aagaattgat gtcagatgac tgactaagtg tgacattgag atgcaggttt aacagatttc   1260
agagatttgg aagtactgga tctcagtttc aatggtgtca atgactctga ggctagtcat   1320
agtgagtggc tgcctttttt tgctttgttt tatggaagtg cttacctctg ctgacttata   1380
acatcactta tgaatgtgtt tcttggtggt gcaggtttaa gtacggcgaa actgaaaaca   1440
ctagatctta atttcaatcc gttgtcagat ttttctcaac ttaaaggtag acagagagta   1500
ccaggggatt tacatacatg atctttatcc atttctgtca actttccaat tataacttgt   1560
gttttcccgg atcttcaggt ttagaaagcc tccaagagtt acaagtcttg aaattacgag   1620
gaaataaatt caaccacacg ctatctactc atggtaagtg ttataaaact gttcttgcag   1680
aagtgactta tggcttaaag aaggcaatca aatgtattct gggttttct cctaagaatg   1740 tttatttgc ctggcagtac tgaaagatct taaaatgttg caagaactgg atctcagtga   1800
caatgggttc acaaatttag atcatggccg aggtaagaca tatatagaaa gtaaaacttg   1860
cttgctctat cctaactggt ttaatctatc tactttaact ttttttcata acgttgatg   1920 agagtagaag tgagaagaga tttgatttta gagaagttgt tcagaaagtc gaggtcagaa   1980
attaaaagtt cagcaagcaa ctatgaagcc tagttttcct gggtatcttc tatagctatt   2040
gtagaccctc tggataggat tgcgtctaag tttccagatg agcataacac accacaagtc   2100
agttactgtg ggaggggtta aagagactag aatcagatta tgataaaata attctggata   2160
ttgtttggtt tggtgtaggt ttttgtggtc aataattgag aataatttcg ttgaatcaat   2220
gtctcattgg tgtgttacat ttgggttggt gaatatagaa cggtttcctg ggttgcttaa   2280
cagtcactta catgcttatt agaagtggag catgcaaatc tttatctatt tatgtatcct   2340
tatgttcttt caactgcagg tttagagatt cctacatctt tacaagtatt ggatttcaaa   2400
agaaatcaat tgtctttgac ccacgaaggt gaatattaca ataatttat ctttcttatc    2460 ttatgcattt tttggtctaa acagaagagt cacactttgg tcaccctcct aactgaattt   2520
atacatagat agattgtgag aacagaagaa cttaatgagt tacatggcta tgaagtctaa   2580
ttagttcata tgatgatgga gttggtgaat atcttgttat tactctcttt taaagatgaa   2640
gttgatgatt attctgattt cttacactct tatttgatta atttcaggct atttagggat   2700
ttgcagacta atgaaactca gggagctgga tttgagcagc aatgctttaa caagtctacc   2760
```

-continued

```
ttattgtttg ggtaacttaa cgcatcttcg aactcttgat ctatcgaaca accaattgaa    2820
tggaaacctg tcttcctttg tgtctggtct accatcagtg cttgagtact tgtcgctgct    2880
tgataataac ttcgacggtt cgttcttgtt caactcactg gtcaatcaaa caagactcac    2940
agtattcaaa ttgtcatcaa aagttggtgt gatccaagtt cagactgaga gttcatgggc    3000
tccattgttt caattgaaga tgttatattt atcgaattgc agtcttggca gcacaatgct    3060
cggctttctc gtgcatcagc gtgacttgtg cttcgttgat ctctctcata caagttgac    3120
aggaacattc ccgacttggc ttgtgaagaa taacacaagg ctgcagacta ttttactaag    3180
tgggaactca ttgacaaagc ttcaactacc tattcttgtt catggcttgc aagttctcga    3240
tatctcgagt aatatgatat atgattcgat tcaagaggac atagggatgg tgtttccaaa    3300
cctgaggttt atgaactttt cttcaaatca ttttcaagga actataccat cttcgattgg    3360
ggagatgaaa agcctacaag tcttggacat gtcttctaat ggtctatatg ggcagctacc    3420
tattatgttt ttaagtggtt gctactcgct aagggttctg aagctctcca acaatcaatt    3480
acagggaaaa atattttcga agcatgcaaa tcttactggt ttagttgggc ttttttcttga    3540
tggcaacaat tttactggga gtcttgaaga gggtttattg aagtcaaaga atcttactct    3600
tttagacata tcagataata ggttttcggg catgcttcca ctttggattg gtaggatatc    3660
aaggcttttcc tacctataca tgagtggtaa tcagctaaaa ggtcctttcc cttttctacg    3720
acagagtcct tgggttgagg ttatggacat ctcacacaat agcttctctg gttcgatacc    3780
aaggaatgtg aattttccat ctctcagaga actaagacta caaaacaatg agtttacggg    3840
tttagttccg ggaaatttat tcaaggctgc gggattagaa gtgcttgatt tgcggaacaa    3900
caattttttct ggaaagatac tgaacactat tgaccagaca tctaagttac gtattcttct    3960
tctacggaat aacagctttc aaacttatat ccctgggaaa atatgtcagc taagtgaagt    4020
tggtctgtta gacttgtctc acaatcaatt cagaggcccc ataccatcat gtttcagtaa    4080
aatgtctttt ggtgcagagc agaatgaccg taccatgtca cttgttgcag attttgactt    4140
ctcatacatt acattcttgc cacattgtca atatggatca catcttaact tggatgatgg    4200
tgtcaggaat ggttatcaac caaaaccagc aaccgtagtg gattttttaa cgaaaagcag    4260
atatgaggcg tatcaaggtg atattctccg ctatatgcat ggtctggatt tgtcgagcaa    4320
cgaactatcg ggtgaaattc caatcgagat tggagatctt cagaatatca ggtccctgaa    4380
tttgtcaagt aaccgcctca caggctccat accagatagc atttcaaagc tgaagggctt    4440
agagagtctt gatctatcca acaataagct agatggaagt atccctcctg cgctagccga    4500
tctcaacagt ttaggatact tgaatatctc atataacaat ttatcaggtg aaatcccttt    4560
caaaggccat cttgttacct tgacgagag gagttacata ggcaacgctc atctctgtgg    4620
acttcctaca aataaaaatt gcatctccca gagagtccct gagccaccaa gtgtgtcaac    4680
gcatgccaaa gaggaagaaa atgaagaaga aggtaatgtg atagacatgg tgtggtttta    4740
ctggacttgt gctgcagtct acatatctac atccttggca ttgtttgctt tcctctacat    4800
agactcacga tggtcccgag aatggtttta tcgtgtagat ctatgcgttc atcatattct    4860
acagttcaag cgttcctcag tctgcaactg a                                    4891
```

<210> SEQ ID NO 3
<211> LENGTH: 1021
<212> TYPE: PRT
<213> ORGANISM: Solanum lycopersicum

<400> SEQUENCE: 3

```
Met Gly Lys Arg Thr Asn Pro Arg His Phe Leu Val Thr Trp Ser Leu
1               5                   10                  15

Leu Leu Leu Glu Thr Ala Phe Gly Leu Thr Ser Arg Glu Val Asn Lys
            20                  25                  30

Thr Leu Cys Ile Glu Lys Glu Arg Gly Ala Leu Leu Glu Phe Lys Arg
            35                  40                  45

Gly Leu Asn Asp Asp Phe Gly Arg Leu Ser Thr Trp Gly Asp Glu Glu
        50                  55                  60

Glu Cys Cys Asn Trp Lys Gly Ile Glu Cys Asp Lys Arg Thr Gly His
65                  70                  75                  80

Val Ile Val Leu Asp Leu His Ser Glu Val Thr Cys Pro Gly His Ala
                85                  90                  95

Cys Phe Ala Pro Ile Leu Thr Gly Lys Val Ser Pro Ser Leu Leu Glu
            100                 105                 110

Leu Glu Tyr Leu Asn Phe Leu Asp Leu Ser Val Asn Gly Phe Glu Asn
        115                 120                 125

Ser Glu Ile Pro Arg Phe Ile Gly Ser Leu Lys Arg Leu Glu Tyr Leu
    130                 135                 140

Asn Leu Ser Ser Ser Asp Phe Ser Gly Glu Ile Pro Ala Gln Phe Gln
145                 150                 155                 160

Asn Leu Thr Ser Leu Arg Ile Leu Asp Leu Gly Asn Asn Leu Ile
            165                 170                 175

Val Lys Asp Leu Val Trp Leu Ser His Leu Ser Ser Leu Glu Phe Leu
            180                 185                 190

Arg Leu Gly Gly Asn Asp Phe Gln Ala Arg Asn Trp Phe Arg Glu Ile
        195                 200                 205

Thr Lys Val Pro Ser Leu Lys Glu Leu Asp Leu Ser Val Cys Gly Leu
    210                 215                 220

Ser Lys Phe Val Pro Ser Pro Ala Asp Val Ala Asn Ser Ser Leu Ile
225                 230                 235                 240

Ser Leu Ser Val Leu His Leu Cys Cys Asn Glu Phe Ser Thr Ser Ser
            245                 250                 255

Glu Tyr Ser Trp Leu Phe Asn Phe Ser Thr Ser Leu Thr Ser Ile Asp
        260                 265                 270

Leu Ser His Asn Gln Leu Ser Arg Gln Ile Asp Asp Arg Phe Gly Ser
    275                 280                 285

Leu Met Tyr Leu Glu His Leu Asn Leu Ala Asn Asn Phe Gly Ala Glu
        290                 295                 300

Gly Gly Val Pro Ser Ser Phe Gly Asn Leu Thr Arg Leu His Tyr Leu
305                 310                 315                 320

Asp Met Ser Asn Thr Gln Thr Tyr Gln Trp Leu Pro Glu Leu Phe Leu
            325                 330                 335

Arg Leu Ser Gly Ser Arg Lys Ser Leu Glu Val Leu Gly Leu Asn Asp
        340                 345                 350

Asn Ser Leu Phe Gly Ser Ile Val Asn Val Pro Arg Phe Ser Ser Leu
    355                 360                 365

Lys Lys Leu Tyr Leu Gln Lys Asn Met Leu Asn Gly Phe Phe Met Glu
        370                 375                 380

Arg Val Gly Gln Val Ser Ser Leu Glu Tyr Leu Asp Leu Ser Asp Asn
385                 390                 395                 400

Gln Met Arg Gly Pro Leu Pro Asp Leu Ala Leu Phe Pro Ser Leu Arg
            405                 410                 415
```

```
Glu Leu His Leu Gly Ser Asn Gln Phe Gln Gly Arg Ile Pro Gln Gly
            420                 425                 430

Ile Gly Lys Leu Ser Gln Leu Arg Ile Phe Asp Val Ser Ser Asn Arg
            435                 440                 445

Leu Glu Gly Leu Pro Glu Ser Met Gly Gln Leu Ser Asn Leu Glu Arg
            450                 455                 460

Phe Asp Ala Ser Tyr Asn Val Leu Lys Gly Thr Ile Thr Glu Ser His
465                 470                 475                 480

Phe Ser Asn Leu Ser Ser Leu Val Asp Leu Asp Leu Ser Phe Asn Leu
            485                 490                 495

Leu Ser Leu Asn Thr Arg Phe Asp Trp Val Pro Pro Phe Gln Leu Gln
            500                 505                 510

Phe Ile Arg Leu Pro Ser Cys Asn Met Gly Pro Ser Phe Pro Lys Trp
            515                 520                 525

Leu Gln Thr Gln Asn Asn Tyr Thr Leu Leu Asp Ile Ser Leu Ala Asn
            530                 535                 540

Ile Ser Asp Met Leu Pro Ser Trp Phe Ser Asn Leu Pro Pro Glu Leu
545                 550                 555                 560

Lys Ile Leu Asn Leu Ser Asn Asn His Ile Ser Gly Arg Val Ser Glu
            565                 570                 575

Phe Ile Val Ser Lys Gln Asp Tyr Met Ile Ile Asp Leu Ser Ser Asn
            580                 585                 590

Asn Phe Ser Gly His Leu Pro Leu Val Pro Ala Asn Ile Gln Ile Phe
            595                 600                 605

Tyr Leu His Lys Asn His Phe Ser Gly Ser Ile Ser Ser Ile Cys Arg
            610                 615                 620

Asn Thr Ile Gly Ala Ala Thr Ser Ile Asp Leu Ser Arg Asn Gln Phe
625                 630                 635                 640

Ser Gly Glu Val Pro Asp Cys Trp Met Asn Met Ser Asn Leu Ala Val
            645                 650                 655

Leu Asn Leu Ala Tyr Asn Asn Phe Ser Gly Lys Val Pro Gln Ser Leu
            660                 665                 670

Gly Ser Leu Thr Asn Leu Glu Ala Leu Tyr Ile Arg Gln Asn Ser Phe
            675                 680                 685

Arg Gly Met Leu Pro Ser Phe Ser Gln Cys Gln Leu Leu Gln Ile Leu
            690                 695                 700

Asp Ile Gly Gly Asn Lys Leu Thr Gly Arg Ile Pro Ala Trp Ile Gly
705                 710                 715                 720

Thr Asp Leu Leu Gln Leu Arg Ile Leu Ser Leu Arg Ser Asn Lys Phe
            725                 730                 735

Asp Gly Ser Ile Pro Ser Leu Ile Cys Gln Leu Gln Phe Leu Gln Ile
            740                 745                 750

Leu Asp Leu Ser Glu Asn Gly Leu Ser Gly Lys Ile Pro Gln Cys Leu
            755                 760                 765

Asn Asn Phe Thr Ile Leu Arg Gln Glu Asn Gly Ser Gly Glu Ser Met
770                 775                 780

Asp Phe Lys Val Arg Tyr Asp Tyr Ile Pro Gly Ser Tyr Leu Tyr Ile
785                 790                 795                 800

Gly Asp Leu Leu Ile Gln Trp Lys Asn Gln Glu Ser Glu Tyr Lys Asn
            805                 810                 815

Ala Leu Leu Tyr Leu Lys Ile Ile Asp Leu Ser Ser Asn Lys Leu Val
            820                 825                 830
```

```
Gly Gly Ile Pro Lys Glu Ile Ala Glu Met Arg Gly Leu Arg Ser Leu
            835                 840                 845
Asn Leu Ser Arg Asn Asp Leu Asn Gly Thr Val Val Glu Gly Ile Gly
        850                 855                 860
Gln Met Lys Leu Leu Glu Ser Leu Asp Leu Ser Arg Asn Gln Leu Ser
865                 870                 875                 880
Gly Met Ile Pro Gln Gly Leu Ser Asn Leu Thr Phe Leu Ser Val Leu
                885                 890                 895
Asp Leu Ser Asn Asn His Leu Ser Gly Arg Ile Pro Ser Ser Thr Gln
            900                 905                 910
Leu Gln Ser Phe Asp Arg Ser Tyr Ser Gly Asn Ala Gln Leu Cys
        915                 920                 925
Gly Pro Pro Leu Glu Glu Cys Pro Gly Tyr Ala Pro Pro Ile Asp Arg
    930                 935                 940
Gly Ser Asn Thr Asn Pro Gln Glu His Asp Asp Asp Glu Phe Ser
945                 950                 955                 960
Ser Leu Glu Phe Tyr Val Ser Met Val Leu Gly Phe Phe Val Thr Phe
                965                 970                 975
Trp Gly Ile Leu Gly Cys Leu Ile Val Asn Arg Ser Trp Arg Asn Ala
            980                 985                 990
Tyr Phe Thr Phe Leu Thr Asp Met  Lys Ser Trp Leu His  Met Thr Ser
        995                 1000                1005
Arg Val  Cys Phe Ala Arg Leu  Lys Gly Lys Leu Arg  Asn
    1010                1015                1020

<210> SEQ ID NO 4
<211> LENGTH: 3066
<212> TYPE: DNA
<213> ORGANISM: Solanum lycopersicum

<400> SEQUENCE: 4
atgggcaaaa gaactaatcc aagacatttc cttgttactt ggtctttact gctcctagag    60
acagctttg gattaacttc aagagaagtt aacaagaccc tttgtataga aaggagaga    120
ggtgccttc ttgagtttaa agaggccctt aacgacgatt ttggtcgttt atctacctgg    180
ggtgatgaag aagaatgctg caattggaag ggtattgaat gtgacaaaag aacaggtcat    240
gttattgttc ttgatctcca cagtgaggtt acttgtccag ccatgcttg ttttgctcca    300
atattgacag gtaaagttag tccttctcta cttgagttgg agtatttgaa tttcttggac    360
ctcagtgtta atggatttga aaatagtgag ataccaagat tcataggctc ccttaagaga    420
ctggagtact taaacctttc atcttctgat ttttctggtg aaattccagc acagttccag    480
aatctaactt ctttgaggat tcttgatctc ggaaacaata atcttatagt aaaggacctt    540
gtgtggcttt ctcatctctc ctctctagaa ttcttgcgcc ttggtggtaa cgatttccaa    600
gcaagaaact ggtttcgaga gataactaag gtccccttcat tgaaagaatt ggacttgagt    660
gtttgtggac tctctaaatt cgttccgtct ccagctgatg tagctaattc atctttgatc    720
tctctttctg ttcttcattt atgttgtaat gagttttcta cttcatctga atatagctgg    780
ttattcaatt ttagcacaag cctaactagc atagaccttt tcataatca actcagtcgt    840
caaattgatg atcgctttgg gagcttgatg tatcttgaac atcttaatct tgctaataat    900
tttggggctg aaggtgggt tccaagttct tttgggaatt tgacacgtct acattatctg    960
gacatgtcta acactcagac ataccaatgg cttcctgagt gtttctcag gttatcaggt   1020
agtaggaaat cacttgaggt tttgggattg aacgacaact cgttgtttgg ttcaattgtt   1080
```

```
aatgtgccaa gattttcatc cttgaagaaa ttatacctgc agaagaatat gctgaatggt    1140 ttttcatgg aaagagtggg acaagtttcg agcctcgagt atctagactt gtctgataac     1200
caaatgagag ggccattacc agatttagca cttttccat cattaagaga gttgcatctt    1260
ggctctaatc aatttcaagg gaggatacca caaggtattg aaaactttc acagcttaga    1320 attttgacg tctcgtccaa tagattagag ggtttaccag aaagtatggg caactatca    1380 aacctggaaa ggtttgatgc ttcttataat gtcctgaagg gtacaatcac agagtcccac    1440
ttttcaaacc tctccagttt agtagactta gacctatcct tcaacttgtt gtctttgaac    1500
acgagattcg attgggttcc tccttttcaa ctacaattta taaggcttcc atcttgcaat    1560
atgggacctt cttttccgaa atggctacaa actcagaata actacactct tcttgatatt    1620
tctcttgcga atatatcaga catgctacca agttggttct ccaatcttcc tcccgagctc    1680
aagattctga atctctctaa caaccacatc agtggcagag tttcggagtt catagtgagt    1740
aaacaagatt acatgattat agatttaagt tctaacaact tttcaggaca tttgccacta    1800
gttcctgcca atatacagat cttttacctt cataaaaatc acttctctgg atccatttct    1860
tccatttgta gaaatacaat aggagctgcc acttccatcg acttgtcacg caaccaattt    1920
tcaggagaag ttcctgattg ttggatgaat atgagtaatc tagctgttct aaatctagcc    1980
tacaacaatt tctccggaaa agttccacaa tcattaggct ccttgacaaa tttggaggcg    2040
ttatacatac gtcagaacag ctttagagga atgttgcctt cttttcaca atgtcagctg    2100 ctgcaaatct tggatattgg agggaataag ttgactggaa gaatcccagc atggataggg    2160
actgacctac tccaattgcg cattctaagc ctacgttcca acaaattcga tggcagcatt    2220
ccatcactta tctgccagct tcaatttctt cagatactgg acctttcaga aaatggatta    2280
tctgggaaaa ttccacagtg cctcaacaac tttaccatat gcgtcaaga aaatggctct    2340 ggtgagtcaa tggattttaa agtccgttat gactatattc caggatctta cttgtacata    2400
ggtgatttac tgattcaatg gaaaaaccag gagtccgagt acaagaatgc tttactatat    2460
ctgaagatca ttgatctttc aagtaataaa ttagttggag gtatccctaa agagatagct    2520
gaaatgagag gattgagatc attgaacctc tcgagaaatg atcttaatgg aactgtcgtt    2580
gaaggaatag gtcaaatgaa gttgttggag tccctcgact tgtcaagaaa ccaactctct    2640
ggcatgatcc ctcagggcct ttctaacttg actttcttta gtgtgttgga cttatcgaac    2700
aaccacttat caggaagaat tccatcaagc actcaactgc agagtttcga tagatcatcc    2760
tatagtggca atgctcaact ctgcggtcct cctcttgaag agtgtcctgg atatgctccc    2820
cctatcgatc gtggaagcaa caccaatcca caagaacatg atgatgatga tgagttctca    2880
tctctggagt tttatgtatc aatggtgcta ggtttcttcg tcacgttctg gggaatttta    2940
ggctgtttga ttgtcaaccg ttcgtggagg aatgcctact tcacattctt aacagacatg    3000
aagagttggc tccatatgac atcaagagtc tgctttgcaa gactgaaggg aaagctaagg    3060
aactga                                                              3066
```

<210> SEQ ID NO 5
<211> LENGTH: 24
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (2)..(3)
<223> OTHER INFORMATION: Xaa is any amino acid

```
<220> FEATURE:
<221> NAME/KEY: MISC_FEATURE
<222> LOCATION: (5)..(6)
<223> OTHER INFORMATION: Xaa is any amino acid
<220> FEATURE:
<221> NAME/KEY: MISC_FEATURE
<222> LOCATION: (8)..(9)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (13)..(14)
<223> OTHER INFORMATION: Xaa is any amino acid
<220> FEATURE:
<221> NAME/KEY: MISC_FEATURE
<222> LOCATION: (16)..(16)
<223> OTHER INFORMATION: Xaa is any amino acid
<220> FEATURE:
<221> NAME/KEY: MISC_FEATURE
<222> LOCATION: (18)..(18)
<223> OTHER INFORMATION: Xaa is any amino acid
<220> FEATURE:
<221> NAME/KEY: MISC_FEATURE
<222> LOCATION: (20)..(20)
<223> OTHER INFORMATION: Xaa is any amino acid
<220> FEATURE:
<221> NAME/KEY: MISC_FEATURE
<222> LOCATION: (23)..(24)
<223> OTHER INFORMATION: Xaa is any amino acid

<400> SEQUENCE: 5

Leu Xaa Xaa Leu Xaa Xaa Leu Xaa Xaa Leu Xaa Leu Xaa Xaa Asn Xaa
1               5                   10                  15

Leu Xaa Gly Xaa Ile Pro Xaa Xaa
            20
```